(12) United States Patent
Uchida et al.

(10) Patent No.: US 7,226,447 B2
(45) Date of Patent: Jun. 5, 2007

(54) ELECTROSURGICAL GENERATOR

(75) Inventors: Andy H. Uchida, Mountain View, CA (US); Duane W. Marion, Santa Clara, CA (US); Ken Woodland, Wilmington, MA (US); Katherine A. Knudsen, San Jose, CA (US)

(73) Assignee: Smith & Nephew, Inc., Memphis, TN (US)

( * ) Notice: Subject to any disclaimer, the term of this patent is extended or adjusted under 35 U.S.C. 154(b) by 464 days.

(21) Appl. No.: 10/873,289

(22) Filed: Jun. 23, 2004

(65) Prior Publication Data

US 2005/0288662 A1 Dec. 29, 2005

(51) Int. Cl.
*A61B 18/18* (2006.01)
(52) U.S. Cl. .......................................... 606/34; 128/898
(58) Field of Classification Search ................ 128/898; 606/34

See application file for complete search history.

(56) References Cited

U.S. PATENT DOCUMENTS

| | | | |
|---|---|---|---|
| 164,184 A | 6/1875 | Kidder | |
| 300,155 A | 6/1884 | Starr | |
| 371,664 A | 10/1887 | Brannan et al. | |
| 452,220 A | 5/1891 | Gunning | |
| 1,314,855 A | 9/1919 | Carpenter | |
| 1,366,756 A | 1/1921 | Wappler | |
| 1,731,627 A | 10/1929 | Johnson et al. | |
| 1,735,271 A | 11/1929 | Groff | |
| 1,814,791 A | 7/1931 | Ende | |
| 1,908,583 A | 5/1933 | Wappler | |
| 1,916,722 A | 7/1933 | Ende | |
| 1,932,258 A | 10/1933 | Wappler | |
| 1,943,543 A | 1/1934 | McFadden | |
| 1,983,669 A | 12/1934 | Kimble | |
| 2,002,594 A | 5/1935 | Wappler et al. | |

(Continued)

FOREIGN PATENT DOCUMENTS

EP 0558297 A2 9/1993

(Continued)

OTHER PUBLICATIONS

Beadling, Lee "Electrosurgery: Sculpting the future of arthroscopy," *Orthopedics Today.*

(Continued)

*Primary Examiner*—Michael Peffley
*Assistant Examiner*—Pete Vrettakos
(74) *Attorney, Agent, or Firm*—Fish & Richardson, P.C.

(57) ABSTRACT

A method includes recognizing an electrosurgical probe coupled to an electrosurgical generator, selecting a mode of the electrosurgical generator based upon the recognized probe, setting a therapy profile based upon the selected mode, and displaying the therapy profile. The generator can include user inputs for modifying the therapy profile. A computer implemented method for achieving a target temperature includes: a) receiving the target temperature; b) calculating a first set temperature; c) commanding a first output power level until a measured temperature is equal to or greater than the first set temperature; d) calculating an updated set temperature based upon the target temperature; e) commanding a second output power level until the measured temperature is equal to or greater than the updated set temperature; and repeating d and e until the updated set temperature is equal to the target temperature.

12 Claims, 9 Drawing Sheets

U.S. PATENT DOCUMENTS

| | | |
|---|---|---|
| 2,004,559 A | 6/1935 | Wappler et al. |
| 2,050,904 A | 8/1936 | Trice |
| 2,056,377 A | 10/1936 | Wappler |
| 2,224,464 A | 12/1940 | Wolf |
| 2,275,167 A | 3/1942 | Bierman |
| 2,888,928 A | 6/1959 | Seiger |
| 3,152,590 A | 10/1964 | Zurdo et al. |
| 3,163,165 A | 12/1964 | Isikawa |
| 3,460,539 A | 8/1969 | Anhalt, Sr. |
| 3,595,239 A | 7/1971 | Petersen |
| 3,768,482 A | 10/1973 | Shaw |
| 3,828,780 A | 8/1974 | Morrison, Jr. |
| 3,870,047 A | 3/1975 | Gonser |
| 3,901,342 A | 8/1975 | Storz |
| 3,902,494 A | 9/1975 | Haberlen et al. |
| 3,920,021 A | 11/1975 | Hiltebrandt |
| 3,920,022 A | 11/1975 | Pastor |
| 3,938,527 A | 2/1976 | Rioux et al. |
| 3,987,795 A | 10/1976 | Morrison |
| 4,024,467 A | 5/1977 | Andrews et al. |
| 4,189,685 A | 2/1980 | Doss |
| 4,196,734 A | 4/1980 | Harris |
| 4,315,510 A | 2/1982 | Kihn |
| 4,318,409 A | 3/1982 | Oosten |
| 4,346,332 A | 8/1982 | Walden |
| 4,346,715 A | 8/1982 | Gammell |
| 4,350,168 A | 9/1982 | Chable et al. |
| 4,378,801 A | 4/1983 | Oosten |
| 4,411,266 A | 10/1983 | Cosman |
| 4,448,198 A | 5/1984 | Turner |
| 4,531,524 A | 7/1985 | Mioduski |
| 4,565,200 A | 1/1986 | Cosman |
| 4,574,801 A | 3/1986 | Manes |
| 4,590,934 A | 5/1986 | Malis et al. |
| 4,597,379 A | 7/1986 | Kihen et al. |
| 4,644,955 A | 2/1987 | Mioduski |
| 4,672,962 A | 6/1987 | Hershenson |
| 4,712,559 A | 12/1987 | Turner |
| 4,727,874 A | 3/1988 | Bowers et al. |
| 4,739,759 A | 4/1988 | Rexroth |
| 4,800,899 A | 1/1989 | Elliott |
| 4,846,196 A | 7/1989 | Wiksell et al. |
| 4,907,589 A | 3/1990 | Cosman |
| 4,920,978 A | 5/1990 | Colvin |
| 4,927,420 A | 5/1990 | Newkirk et al. |
| 4,938,761 A | 7/1990 | Ensslin |
| 4,955,377 A | 9/1990 | Lennox et al. |
| 4,966,597 A | 10/1990 | Cosman |
| 4,974,587 A | 12/1990 | Turner et al. |
| 4,979,948 A | 12/1990 | Geddes et al. |
| 5,003,991 A | 4/1991 | Takayama et al. |
| 5,097,844 A | 3/1992 | Turner |
| 5,103,804 A | 4/1992 | Abele et al. |
| 5,106,360 A | 4/1992 | Ishiwara et al. |
| 5,122,137 A | 6/1992 | Lennox |
| 5,151,100 A | 9/1992 | Abele et al. |
| 5,190,540 A | 3/1993 | Lee |
| 5,191,883 A | 3/1993 | Lennox et al. |
| 5,209,233 A | 5/1993 | Holland et al. |
| 5,224,492 A | 7/1993 | Takahashi et al. |
| 5,249,585 A | 10/1993 | Turner et al. |
| 5,277,201 A | 1/1994 | Stern |
| 5,277,696 A | 1/1994 | Hagen |
| 5,281,218 A | 1/1994 | Imran |
| 5,304,214 A | 4/1994 | DeFord et al. |
| 5,318,525 A | 6/1994 | West et al. |
| 5,318,563 A | 6/1994 | Malis et al. |
| 5,334,193 A | 8/1994 | Nardella |
| 5,342,357 A | 8/1994 | Nardella |
| 5,344,435 A | 9/1994 | Turner et al. |
| 5,348,554 A | 9/1994 | Imran et al. |
| 5,352,868 A | 10/1994 | Denen et al. |
| 5,366,490 A | 11/1994 | Edwards et al. |
| 5,370,645 A | 12/1994 | Klicek et al. |
| 5,370,675 A | 12/1994 | Edwards et al. |
| 5,383,874 A | 1/1995 | Jackson et al. |
| 5,383,917 A | 1/1995 | Desai et al. |
| 5,419,767 A | 5/1995 | Eggers et al. |
| 5,421,819 A | 6/1995 | Edwards et al. |
| 5,423,808 A | 6/1995 | Edwards et al. |
| 5,431,649 A | 7/1995 | Mulier et al. |
| 5,433,708 A | 7/1995 | Nichols et al. |
| 5,433,739 A | 7/1995 | Sluijter et al. |
| 5,433,740 A | 7/1995 | Yamaguchi |
| 5,437,662 A | 8/1995 | Nardella |
| 5,437,664 A | 8/1995 | Cohen et al. |
| 5,443,463 A | 8/1995 | Stern et al. |
| 5,443,470 A | 8/1995 | Stern et al. |
| 5,456,682 A | 10/1995 | Edwards et al. |
| 5,458,596 A | 10/1995 | Lax et al. |
| 5,480,397 A | 1/1996 | Eggers et al. |
| 5,480,398 A | 1/1996 | Eggers et al. |
| 5,484,400 A | 1/1996 | Edwards et al. |
| 5,496,312 A | 3/1996 | Klicek |
| 5,505,730 A | 4/1996 | Edwards |
| 5,514,129 A | 5/1996 | Smith |
| 5,514,130 A | 5/1996 | Baker |
| 5,540,681 A | 7/1996 | Strul et al. |
| 5,540,682 A | 7/1996 | Gardner et al. |
| 5,542,915 A | 8/1996 | Edwards et al. |
| RE35,330 E | 9/1996 | Malone et al. |
| 5,562,720 A | 10/1996 | Stern et al. |
| 5,569,242 A | 10/1996 | Lax et al. |
| 5,573,533 A | 11/1996 | Strul |
| 5,578,008 A | 11/1996 | Hara |
| 5,584,830 A | 12/1996 | Ladd et al. |
| 5,626,575 A | 5/1997 | Crenner |
| 5,628,771 A | 5/1997 | Mizukawa et al. |
| 5,643,255 A | 7/1997 | Organ |
| 5,688,267 A | 11/1997 | Panescu et al. |
| 5,697,925 A | 12/1997 | Taylor |
| 5,697,927 A | 12/1997 | Imran et al. |
| 5,743,903 A | 4/1998 | Stern et al. |
| 5,786,705 A | 7/1998 | Bui et al. |
| 5,843,075 A | 12/1998 | Taylor |
| 5,871,481 A | 2/1999 | Kannenberg et al. |
| 5,931,835 A | 8/1999 | Mackey |
| 5,954,719 A | 9/1999 | Chen et al. |
| 6,045,532 A | 4/2000 | Eggers et al. |
| 6,047,700 A | 4/2000 | Eggers et al. |
| 6,073,051 A | 6/2000 | Sharkey et al. |
| 6,074,386 A | 6/2000 | Goble et al. |
| 6,086,581 A | 7/2000 | Reynolds et al. |
| 6,095,149 A | 8/2000 | Sharkey et al. |
| 6,099,514 A | 8/2000 | Sharkey et al. |
| 6,099,524 A | 8/2000 | Lipson et al. |
| 6,117,109 A | 9/2000 | Eggers et al. |
| 6,122,549 A | 9/2000 | Sharkey et al. |
| 6,126,682 A | 10/2000 | Sharkey et al. |
| 6,135,999 A | 10/2000 | Fanton et al. |
| 6,142,992 A | 11/2000 | Cheng et al. |
| 6,149,620 A | 11/2000 | Baker et al. |
| 6,162,217 A | 12/2000 | Kannenberg et al. |
| 6,235,020 B1 | 5/2001 | Cheng et al. |
| 6,261,311 B1 | 7/2001 | Sharkey et al. |
| 6,266,551 B1 | 7/2001 | Osadchy et al. |
| 6,296,636 B1 | 10/2001 | Cheng et al. |
| 6,322,549 B1 | 11/2001 | Eggers et al. |
| 6,355,032 B1 | 3/2002 | Hovda et al. |
| 6,391,025 B1 | 5/2002 | Weinstein et al. |
| 6,409,722 B1 | 6/2002 | Hoey et al. |
| 6,461,350 B1 | 10/2002 | Underwood et al. |
| 6,488,679 B1 | 12/2002 | Swanson et al. |
| 6,602,248 B1 | 8/2003 | Sharps et al. |

| | | |
|---|---|---|
| 6,719,754 B2 | 4/2004 | Underwood et al. |
| 6,726,684 B1 | 4/2004 | Woloszko et al. |
| 2001/0029369 A1 | 10/2001 | Kannenberg et al. |
| 2003/0016014 A1 | 1/2003 | Frederick et al. |
| 2003/0060818 A1 | 3/2003 | Kannenberg et al. |

FOREIGN PATENT DOCUMENTS

| | | |
|---|---|---|
| GB | 2160102 | 12/1985 |
| WO | WO 94/10925 | 5/1994 |
| WO | WO 95/09576 | 4/1995 |
| WO | WO 95/09577 | 4/1995 |
| WO | WO 95/24160 | 9/1995 |
| WO | WO 95/25472 | 9/1995 |
| WO | WO 96/00036 | 1/1996 |
| WO | WO 96/00039 | 1/1996 |
| WO | WO 96/00040 | 1/1996 |
| WO | WO 96/00528 | 1/1996 |
| WO | WO 96/34569 | 11/1996 |
| WO | WO 96/39089 | 12/1996 |
| WO | WO 96/39967 | 12/1996 |
| WO | WO 02/32333 | 4/2002 |

OTHER PUBLICATIONS

Bradley, James et al "Monopolar ElectroThermal Capsulorrhapyh," *Applications in Electrothermal Arthroscopy*, Case Report No. S2.

Davis, Robert "New shoulder surgery puts Shark back in the swing," *USA Today*, A11-A12, 1998.

Fanton, Gary S. "Monopolar Electrothermal Arthroscopy For Treatment of Shoulder Instability in the Athlete," *Operative Techniques in Sports Medicine*, vol. 8, No. 3 (Jul. 2000), pp. 242-249.

Lopez, Mandi J. et al. "The Effect of Radiofrequency Energy on the Ultrastructure of Joint Capsular Collagen," *Arthroscopy: The Journal of Arthroscopic and Related Surgery*, vol. 14, No. 5 (Jul.-Aug. 1998), pp. 495-501.

Philippon, Marc J. "Arthroscopic Partial Labrectomy and Thermal Synovectomy Utilizing Monpolar RF Energy Case Report," *Applications in Electrothermal Arthroscopy*, Case Report No. H1.

Sluyter, Menno E. "Radiofrequency Lesions in the Treatment of Cervial Pain Syndromes," *Radionics*, pp. 1-24, 1990.

"Tissue Temperature Control ElectroThermal Arthroscopy Probe," *TAC-C II*, 2000.

*Temperature Matters*, 1998.

Leonard J. Malis, M.D., "Electrosurgery," Technical notes. J. Neurosurg., vol. 85, Nov. 1996, pp. 970-975.

"Special Use For Treatment of Telangiectasia, Portwine Stain, Hairy Nevus, as well as for Epilation Without Hair Regrowth," Innovation by IME, pp. 57-104.

"What's New in Office Electrosurgery? Radiosurgery!", Ellman International Manufacturing Inc., 18 pages.

"Electroshock Therapy", pp. 1180-1202.

ELECTROSURGICAL GENERATOR

TECHNICAL FIELD

This description relates to electrosurgical generators.

BACKGROUND

Lower back pain is a common ailment and affects many people at some point in their lives. Frequently, this pain is the result of cracks or fissures that develop in the wall of the intervertebral disc. These fissures are filled with small nerve endings and blood vessels, and often are a chronic source of pain. Additionally, the inner disc tissue (nucleus) frequently bulges (herniates) into these fissures in the outer region of the disc, likewise stimulating pain sensors within the disc.

Electrosurgical procedures provide minimally invasive treatment options for treating lower back pain by applying thermal energy (i.e., heat) to the affected area. Electrosurgical procedures have been developed for use in other pain management procedures, such as denervation procedures. An electrosurgical generator provides electrical energy, such as, for example, high frequency and radio frequency electrical energy. In particular, the electrical energy provided by the electrosurgical generator is used in pain management procedures to modify the structure of tissue.

SUMMARY

The electrosurgical generator can be used, for example, to provide radio-frequency (RF) energy for localized tissue coagulation, cutting, ablation, and to create lesions in nervous tissue. The generator is, e.g., a line-powered radio-frequency generator capable of delivering up to approximately 20 watts of power. The generator can provide controls for line power, RF power, setting temperature and/or power, for selecting preset temperature and power combinations, and for selecting programmed treatment profiles. The generator can have a display to display the desired probe and tissue temperature, measured probe impedance, actual probe and/or tissue temperature, delivered power, treatment time, mode setting, preset selection, and messages, and indicators for RF Power On, Stimulation On, and Fault Condition. The software for the generator can be upgraded using a special card.

The generator can include the ability to generate low frequency pulses to stimulate nerves and to assist in the proper placement of the electrosurgical probe in the location that is causing pain. For example, the generator may include the ability to generate low frequency pulses of 0.1 to 3 ms in duration at a frequency between approximately 2–50 hz.

Temperature and impedance monitoring can be used to assist the surgeon by automatically adjusting energy delivery to maintain effective tissue heating during temperature control applications. Preset temperature and power settings can offer the convenience of quickly configuring the generator for use. Programmed temperature profiles can provide the convenience of selecting a treatment setting for use with a particular type of probe, for example, the Smith and Nephew SPINECATH® Intradiscal Catheter, the Smith and Nephew Decompression Catheter, and the Smith & Nephew RF Denervation Probe.

In one general aspect, a method includes recognizing an electrosurgical probe coupled to an electrosurgical generator, selecting a mode of the electrosurgical generator based upon the recognized probe, setting a therapy profile based upon the selected mode, and displaying the therapy profile. The generator can include user inputs for modifying the therapy profile.

Implementations may include one or more of the following features:

Setting the therapy profile includes automatically setting a default parameters for the selected mode. The therapy profile includes an automatic temperature profile, such as a temperature rise from an initial temperature to a peak temperature and a dwell time at the peak temperature. The temperature rise is, e.g., a fixed rate of temperature rise such as one degree Celsius per thirty seconds, one degree Celsius per six seconds, or one degree Celsius per eighteen seconds. Alternatively, the temperature rise is discontinuous. The rate of temperature rise is selected automatically. The initial temperature, the peak temperature and/or the dwell time at the peak temperature is selected automatically and also can be manually overridden.

In one implementation, the therapy profile includes a frequency parameter and a pulsewidth parameter. The therapy profile also can include an adjustable voltage parameter. A rotary encoder knob that is configured to adjust the voltage parameter can be used.

In another implementation, the therapy profile is switched between a first therapy profile and a second therapy profile. A user modified parameter may be retained when switching between the first therapy profile and the second therapy profile. The therapy profile includes a temperature parameter and a time duration parameter, and also can include a frequency parameter, a pulsewidth parameter, and/or an amplitude parameter. The frequency parameter, the pulsewidth parameter, and/or the amplitude parameter can be adjusted to control a tissue temperature. The pulsewidth may be, for example, 20 ms. In one implementation, the frequency parameter and/or the amplitude parameter are adjusted to control tissue temperature and the pulse width parameter is not adjustable.

The display of at least a portion of the display of the therapy profile can be updated. The therapy profile can be modified, and the modified therapy profile can be displayed.

In another general aspect, a computer program stored on a computer readable medium includes instructions for recognizing an electrosurgical probe coupled to an electrosurgical generator, selecting a mode of the electrosurgical generator based upon the recognized probe, setting a therapy profile based upon the selected mode, and displaying the therapy profile. The generator can include user inputs for modifying the therapy profile.

In another general aspect, a computer implemented method for achieving a target temperature includes: a) receiving the target temperature; b) calculating a first set temperature; c) commanding a first output power level until a measured temperature is equal to or greater than the first set temperature; d) calculating an updated set temperature based upon the target temperature; e) commanding a second output power level until the measured temperature is equal to or greater than the updated set temperature; and repeating d and e until the updated set temperature is equal to the target temperature.

Implementations may include one or more of the following features:

Receiving the target temperature can include retrieving the target temperature from a storage location and receiving the target temperature can include receiving a user input. Calculating the first set temperature can include subtracting a predetermined value from the target temperature or retrieving a pre-stored value. The first power output level can be a maximum power output level, and the second power output level can be a power output level less than the maximum power output level. The maximum power output level can be a maximum output power level for a particular probe being used. In another implementation, the maximum output power level can be the maximum power output level of the generator. In other implementations, the maximum output power level can be a different pre-determined value or a dynamically calculated value. The first output power level can be an output power level based upon an identity of a surgical probe. The first power output level can be greater than the second power output level. Calculating the updated set temperature can include subtracting a predetermined value from the target temperature, adding a predetermined value to the first set temperature, or retrieving a pre-stored value.

In another implementation, a proportional-integral routine can be used to control to the target temperature by adjusting the output voltage.

In another general aspect, a computer program stored on a computer readable medium includes instructions for: a) receiving a target temperature; b) calculating a first set temperature; c) commanding a first output power level until a measured temperature is equal to or greater than the first set temperature; d) calculating an updated set temperature based upon the target temperature; e) commanding a second output power level until the measured temperature is equal to or greater than the updated set temperature; and repeating d and e until the updated set temperature is equal to the target temperature.

In another general aspect, an electrosurgical generator includes means for recognizing an electrosurgical probe, means for selecting a mode of the electrosurgical generator based upon the recognized probe and for setting a therapy profile based upon the selected mode, means for displaying the therapy profile, and means for modifying the therapy profile.

Implementations can include one or more of the following features:

The means for recognizing the electrosurgical probe can include a probe recognition circuit. The means for selecting the mode and for setting the therapy profile can include a processor. The means for displaying the therapy profile can include a visual display, such as, for example, an LCD display. The means for modifying the therapy profile can include a user control, such as, for example, a soft key, an arrow key, or a rotary encoder knob.

In another general aspect, an electrosurgical generator includes a probe recognizing circuit configured to recognize an electrosurgical probe, a processor configured to select a mode of the electrosurgical generator based upon the recognized probe and to set a therapy profile based upon the selected mode, a display configured to display the therapy profile, and a user control configured to modify the therapy profile.

Implementations can include one or more of the following features:

The display can include a visual display, such as, for example, an LCD display. The user control may include, for example, a soft key, an arrow key, or a rotary encoder knob.

In another general aspect, an electrosurgical generator includes means for receiving a target temperature, calculating a first set temperature, commanding a first output power level until a measured temperature is equal to or greater than the first set temperature, calculating an updated set temperature based upon the target temperature, commanding a second output power level until the measured temperature is equal to or greater than the updated set temperature, and determining whether the updated set temperature is equal to the target temperature, and means for modifying the target temperature.

Implementations can include one or more of the following features:

The means for receiving the target temperature, calculating a first set temperature, commanding a first output power level until a measured temperature is equal to or greater than the first set temperature, calculating an updated set temperature based upon the target temperature, commanding a second output power level until the measured temperature is equal to or greater than the updated set temperature, and determining whether the updated set temperature is equal to the target temperature can include a processor. In one implementation, the processor is configured to retrieve the target temperature from a storage location. In another implementation, the processor is configured to receive the target temperature from a user input.

In one implementation, the processor is configured to subtract a predetermined value from the target temperature to obtain the first set temperature. In another implementation, the processor is configured to retrieve a pre-stored value of the first set temperature. In one implementation, the processor is configured to subtract a predetermined value from the target temperature to obtain the updated set temperature. In another implementation, the processor is configured to add a predetermined value to the first set temperature to obtain the updated set temperature. In yet another implementation, the processor is configured to retrieve a pre-stored value of the updated set temperature. The first power output level can be greater than the second power output level, and the means for modifying the target temperature can include a user control.

In another implementation, the set temperature is not ramped to the target temperature. Instead, the measured temperature is controlled directly to achieve the target temperature. The set temperature is not changed or updated. A proportional-integral routine, or other similar routine, can be used to control to the target temperature by adjusting the output voltage.

In another implementation, a first output power can be commanded if the measured temperature is less than a specified value below the target temperature. Once the measured temperature is within the specified value of the target temperature, a control routine, such as a PID or a PI routine, can be used to calculate a second output level for the generator.

In another general aspect, an electrosurgical generator includes a processor configured to receive the target temperature, calculate a first set temperature, command a first output power level until a measured temperature is equal to or greater than the first set temperature, calculate an updated set temperature based upon the target temperature, command a second output power level until the measured temperature is equal to or greater than the updated set temperature, and determine whether the updated set temperature is equal to the target temperature.

Implementations can include one or more of the following features:

The processor can be configured to retrieve the target temperature from a storage location or receive the target temperature from a user input. The processor can configured to calculate the first set temperature by subtracting a predetermined value from the target temperature or by retrieving a pre-stored value. The processor can be configured to calculate the updated set temperature by subtracting a predetermined value from the target temperature, by adding a predetermined value to the first set temperature, or by retrieving a pre-stored value.

The first power output level can be greater than the second power output level. The generator can include a user control configured to modify the target temperature.

In another general aspect, a computer program stored on a computer readable medium includes instructions for: a) receiving a target temperature; b) commanding a first output power level until a measured temperature is within a specified value of the target temperature; c) calculating a second output power level when the measured temperature is within the specified value of the target temperature; d) commanding the second output power level; and repeating c and d until the measured temperature is equal to the target temperature.

Implementations can include one or more of the following features:

The instructions for receiving the target temperature can include instructions for receiving a user input. The first output power level can include a maximum output power level. The maximum output power level can include a maximum output power level based upon an identity of a surgical probe. The second output power level can include a output power level less than the maximum output power level. The first output power level can be an output power level based upon an identity of a surgical probe. The first output power level can be greater than the second output power level. The instructions for calculating the second output power level can include instructions for using a PID algorithm or a PI algorithm to calculate the second output power level. The instructions can also include instructions for receiving an initial second output power level. The instructions for receiving an initial second output power level can include instructions for retrieving the initial second output power level from a storage location. The initial second output power level can be based upon an identity of a surgical probe. The instructions for calculating the second output power level c can include instructions for retrieving a pre-stored value.

In another general aspect, a method for achieving a target temperature includes: a) receiving a target temperature; b) commanding a first output power level until a measured temperature is within a specified value of the target temperature; c) calculating a second output power level when the measured temperature is within the specified value of the target temperature; d) commanding the second output power level; and repeating c and d until the measured temperature is equal to the target temperature.

In another general aspect, an electrosurgical generator can include means for receiving a target temperature, commanding a first output power level until a measured temperature is within a specified value of the target temperature, calculating a second output power level when the measured temperature is within the specified value of the target temperature, commanding the second output power level, and determining whether the measured temperature is equal to the target temperature and means for modifying the target temperature.

Implementations can include one or more of the following features:

The means for receiving a target temperature, commanding a first output power level until a measured temperature is within a specified value of the target temperature, calculating a second output power level when the measured temperature is within the specified value of the target temperature, commanding the second output power level, and determining whether the measured temperature is equal to the target temperature can include a processor.

In another general aspect, an electrosurgical generator can include a processor configured to receive a target temperature, command a first output power level until a measured temperature is within a specified value of the target temperature, calculate a second output power level when the measured temperature is within the specified value of the target temperature, command the second output power level, and determine whether the measured temperature is equal to the target temperature.

Implementations can include one or more of the following features:

The processor can be configured to retrieve the target temperature from a storage location. The processor can be configured to receive the target temperature from a user input. The first output power level can include an output power level based upon an identity of a surgical probe. The first output power level can be greater than the second output power level. The electrosurgical generator can include a user control configured to modify the target temperature.

In another general aspect, a computer program stored on a computer readable medium includes instructions for: a) receiving a target temperature; b) receiving a first generator output setting corresponding to a first generator output power; c) commanding the first generator output setting when a difference between the target temperature and a measured temperature is greater than a specified value; d) calculating a second generator output setting if the first generator output power is less than a maximum allowed generator output power for an identified surgical probe and if the difference between the target temperature and the measured temperature is greater than the specified value, wherein the second generator output setting corresponds to a second generator output power that is greater than the first generator output power, and commanding the second generator output setting; e) calculating a third generator output setting if the first generator output power is greater than the maximum allowed generator output power for the identified surgical probe and the difference between the target temperature and the measured temperature is greater than the specified value, wherein the third generator output setting corresponds to a third generator output power that is less than the first generator output power, and commanding the third generator output setting; and f) repeating c through e until the difference between the target temperature and the measured temperature is less than or equal to the specified value.

Implementations can include one or more of the following features:

The instructions for receiving the target temperature can include instructions for receiving a user input. The instructions for calculating the second generator output setting can include instructions for adding a predetermined value to the first generator output setting. The instructions for calculating the third generator output setting can include instructions for subtracting a predetermined value from the first generator output setting.

The computer program can further include instructions for: g) calculating a fourth generator output setting corresponding to a fourth generator output power if the difference between the target temperature and the measured temperature is less than or equal to the specified value; and h) commanding the fourth generator output setting. Instructions for calculating the fourth generator output setting can include instructions for calculating the fourth generator output setting using a control algorithm. The control algorithm can include setting the fourth generator output setting equal to a first constant multiplied by an integral of an error value plus a second constant multiplied by the error value, wherein the first constant and the second constant are defined for an identified surgical probe and the error value equals the target temperature minus the measured temperature.

The computer program can further include instructions for limiting the fourth generator output control setting to a maximum value. The maximum value can include the first generator output control setting. The computer program can include instructions for not integrating the error value when the fourth generator control setting is equal to the maximum value. The computer program can include instructions for limiting the fourth generator output control setting to a minimum value. The minimum value can be zero.

In another general aspect, a method for achieving a target temperature includes: a) receiving a target temperature; b) receiving a first generator output setting corresponding to a first generator output power; c) commanding the first generator output setting when a difference between the target temperature and a measured temperature is greater than a specified value; d) calculating a second generator output setting if the first generator output power is less than a maximum allowed generator output power for an identified surgical probe and if the difference between the target temperature and the measured temperature is greater than the specified value, wherein the second generator output setting corresponds to a second generator output power that is greater than the first generator output power, and commanding the second generator output setting; e) calculating a third generator output setting if the first generator output power is greater than the maximum allowed generator output power for the identified surgical probe and the difference between the target temperature and the measured temperature is greater than the specified value, wherein the third generator output setting corresponds to a third generator output power that is less than the first generator output power, and commanding the third generator output setting; and f) repeating c through e until the difference between the target temperature and the measured temperature is less than or equal to the specified value.

In another general aspect, an electrosurgical generator includes: means for receiving a target temperature, receiving a first generator output setting corresponding to a first generator output power, commanding the first generator output setting when a difference between the target temperature and a measured temperature is greater than a specified value, calculating a second generator output setting if the first generator output power is less than a maximum allowed generator output power for an identified surgical probe and if the difference between the target temperature and the measured temperature is greater than the specified value, wherein the second generator output setting corresponds to a second generator output power that is greater than the first generator output power, and commanding the second generator output setting, calculating a third generator output setting if the first generator output power is greater than the maximum allowed generator output power for the identified surgical probe and the difference between the target temperature and the measured temperature is greater than the specified value, wherein the third generator output setting corresponds to a third generator output power that is less than the first generator output power, and commanding the third generator output setting and determining whether the difference between the target temperature and the measured temperature is less than or equal to the specified value; and means for modifying the target temperature.

In another general aspect, an electrosurgical generator includes a processor configured to: receive a target temperature; receive a first generator output setting corresponding to a first generator output power; command the first generator output setting when a difference between the target temperature and a measured temperature is greater than a specified value; calculate a second generator output setting if the first generator output power is less than a maximum allowed generator output power for an identified surgical probe and if the difference between the target temperature and the measured temperature is greater than the specified value, wherein the second generator output setting corresponds to a second generator output power that is greater than the first generator output power, and command the second generator output setting; calculate a third generator output setting if the first generator output power is greater than the maximum allowed generator output power for the identified surgical probe and the difference between the target temperature and the measured temperature is greater than the specified value, wherein the third generator output setting corresponds to a third generator output power that is less than the first generator output power, and command the third generator output setting; and determine whether the difference between the target temperature and the measured temperature is less than or equal to the specified value.

Implementations can include one or more of the following:

The processor can be configured to retrieve the target temperature from a storage location. The processor can be configured to receive the target temperature from a user input.

Other features will be apparent from the description and drawings, and from the claims.

DETAILED DESCRIPTION

Figure 1:
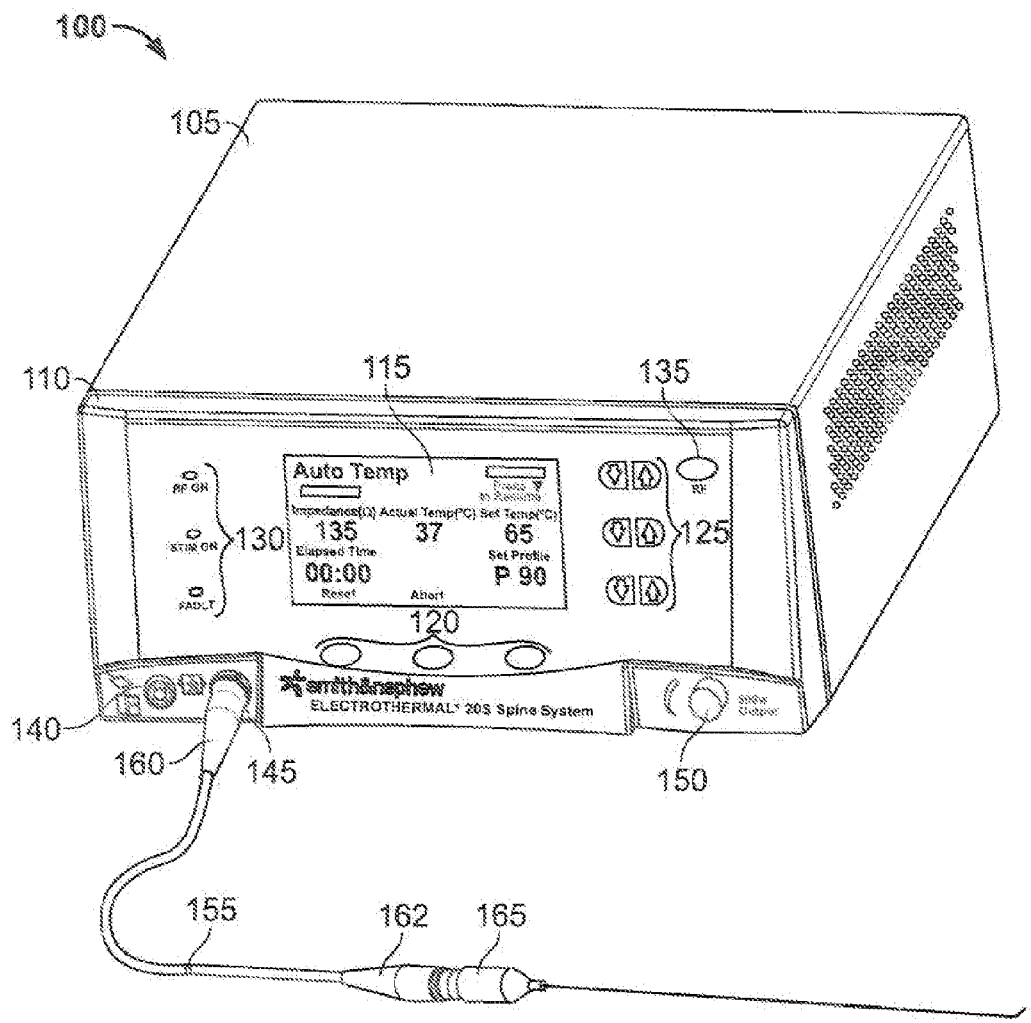
FIG. 1 is a perspective view of an electrosurgical generator.

As shown in FIG. 1, an electrosurgical generator 100 includes a chassis 105, and a front panel 110. The front panel 110 includes a display 115, soft keys 120, arrow keys 125, status indicators 130, an RF output on/off control button 135, a grounding pad receptacle 140, a probe receptacle 145, and a rotary encoder knob 150. Probe receptacle 145 receives a probe 165 via a cable plug 160, a cable 155, and a cable plug 162. The display 115 is, for example, an LCD screen that displays certain information during a surgical procedure, as will be discussed in more detail below with respect to FIGS. 2–3 and 5–10.

Generator 100 can be used with probes such as, for example, the Smith and Nephew SPINECATH® Intradiscal Catheter, the Smith and Nephew Decompression Catheter, and the Smith & Nephew RF Denervation Probe. The electrosurgical generator 100 is capable of therapy profiles through several modes of operation, including SPINECATH® AUTOTEMP® (automatic temperature) mode, Decompression AUTOTEMP® mode, stimulation mode, RF lesion mode, and Pulsed RF mode. When using the Smith & Nephew RF Denervation Probe, the generator initially enters the stimulation mode, and the RF lesion mode or Pulse RF mode is accessed through the stimulation mode.

During a disc denervation procedure, the rotary encoder knob 150 is used to turn on/off the stimulation mode output voltage and adjust the stimulation mode output voltage for motor and sensory stimulus prior to applying RF energy to treat tissue. The rotary encoder knob is pushed to turn the stimulation mode power on or off. With the stimulation mode power on, the rotary encoder knob 150 can be rotated clockwise to increase the stimulation mode output voltage and counter clockwise to decrease the stimulation mode output voltage.

In all modes other than stimulation mode, the RF output on/off control button 135 is used to start or stop RF power delivery. The button 135 is pressed, or alternatively, a foot switch (not shown) is pressed, to start and stop RF power delivery. If the RF output on/off control button 135 is pressed in succession, then RF power delivery toggles on and off.

Figure 2:
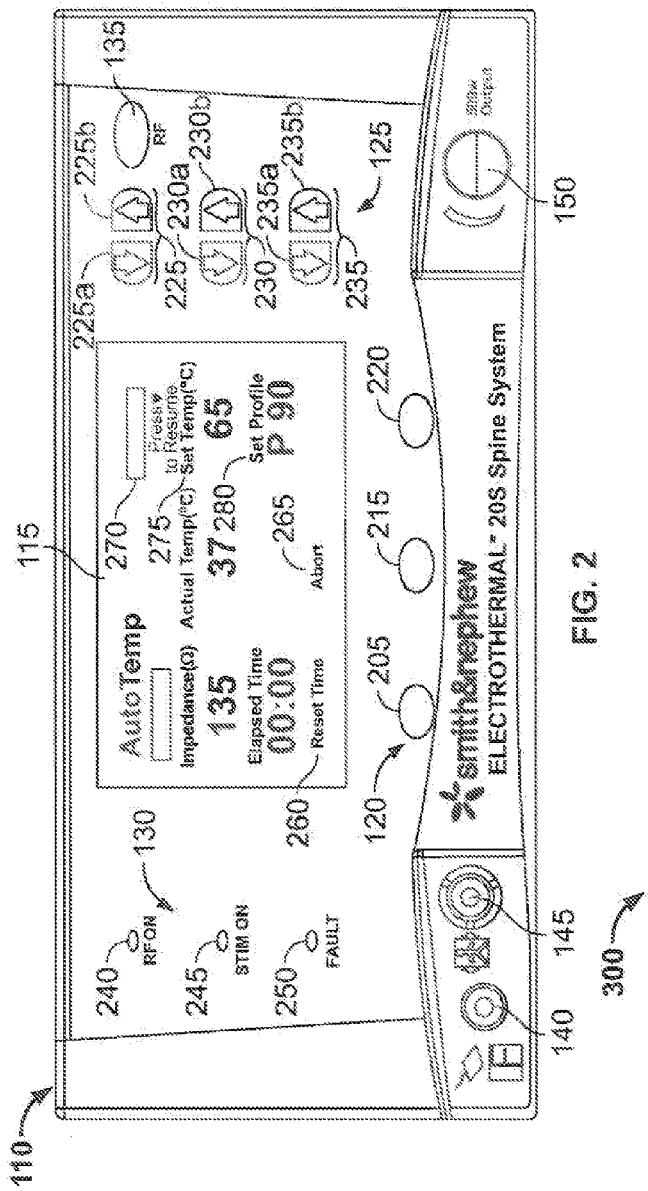
FIG. 2 is a plan view of a front panel of the electrosurgical generator of FIG. 1.

Referring to FIG. 2, the status indicators 130 include an indication for "RF On" such as an LED 240 that is illuminated when the electrosurgical generator 100 is delivering RF power in all modes but the stimulation mode, a "Stimulation On" indication such as an LED 245 that is illuminated when the generator 100 is delivering stimulation power, and a fault indication such as an LED 250 that is illuminated when a fault condition is detected. The arrow keys 125 and soft keys 120 are used to control different parameters for different modes of operation of the generator 100. The soft keys and arrow keys are associated with controls shown in the display 115. The operator manipulates a control by operating the soft key or arrow key corresponding to the control. Typically, the function associated with the soft key can change as the display is changed, and the arrow keys are used to adjust a particular parameter up or down.

As shown, the soft keys 120 include three separate soft keys 205, 215, and 220. Soft key 205 operates on control 260 and soft key 215 operates on control 265. In the implementation shown in FIG. 2, soft key 220 does not have a corresponding control shown in the display 115. Arrow keys 125 include three sets of arrow keys 225, 230, and 235. Arrow keys 225 include a down arrow key 225a and an up arrow key 225b. Arrow keys 230 include a down arrow key 230a and an up arrow key 230b. Arrow keys 235 include a down arrow key 235a and an up arrow key 235b. The arrow keys 225, 230, and 235 operates on controls 280, 275, and 270 of display 115, respectively.

Figure 3:
FIG. 3 is an exemplary standby mode interface implemented by the electrosurgical generator of FIG. 1 while executing the processes of FIGS. 4, 11, 12, and 13.

When line power is initially applied to the generator 100, the generator performs a system self-test to determine if it is performing properly. After the self-test, the generator 100 enters a standby mode in which RF power cannot be delivered. In the standby mode, a user interface (UI), such as the UI 300 shown in FIG. 3, is displayed to the user on display 115. To exit standby mode, a start control 305 is displayed on the user interface 300 after a probe 165 is connected to the generator. The start control 305 is activated by depressing soft key 220. When activated, the start control 305 causes the generator 100 to exit the standby mode and enter an appropriate operating mode as described below.

Figure 4:
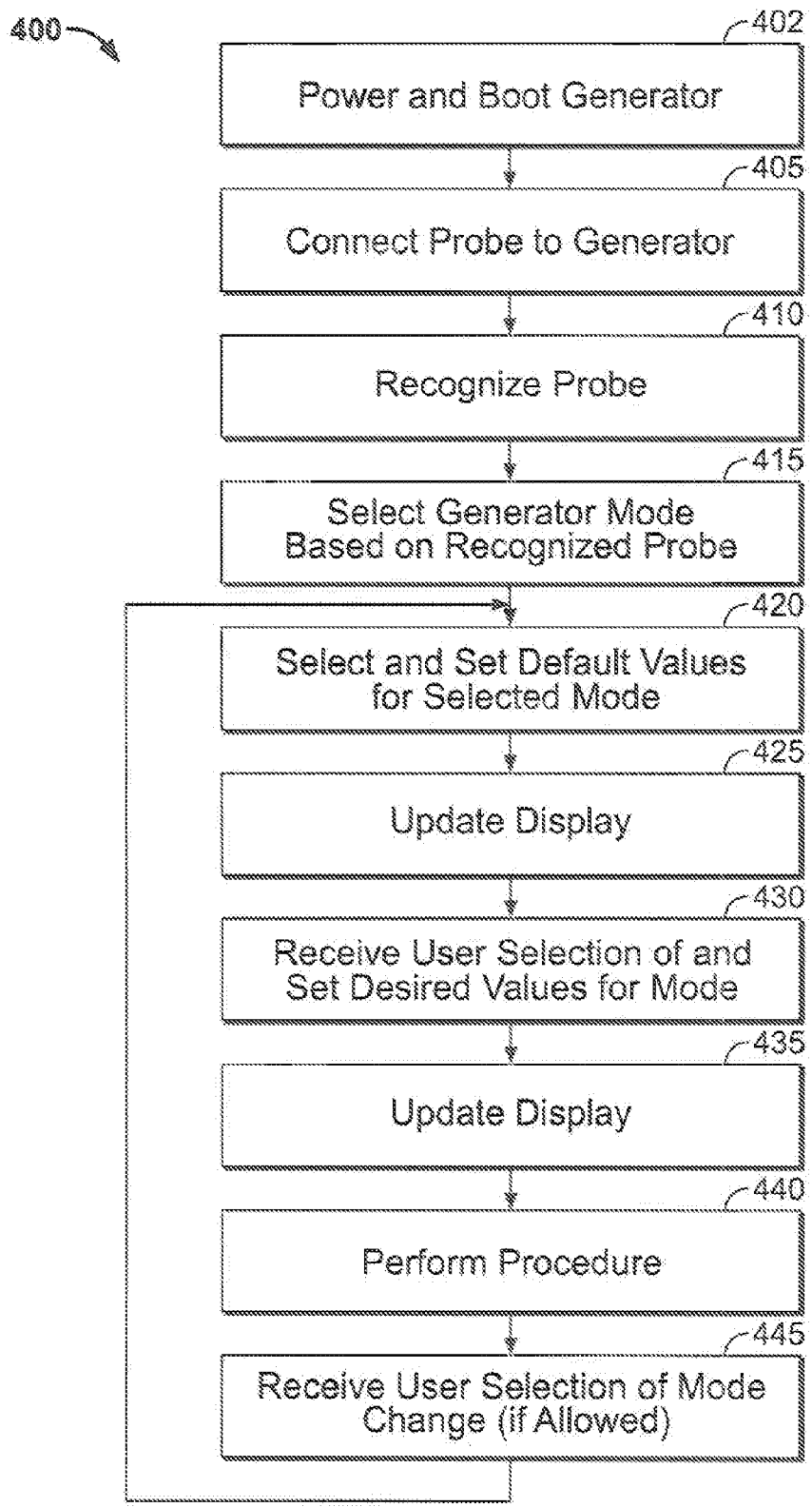
FIGS. 4, 11, 12, and 13 are flow charts of exemplary processes implemented by the electrosurgical generator of FIG. 1.

FIG. 4 shows an exemplary procedure 400 employed using the electrosurgical generator 100 discussed above with respect to FIGS. 1 and 2. After the operator powers up the generator 100 and the generator 100 boots (step 402), the operator connects a probe 165 to the generator 100 (step 405) and depresses soft key 220 to activate the start control 305. The generator 100 recognizes the probe (step 410) and selects a desired mode based on the recognized probe (step 415). For example, if the recognized probe is a SPINECATH®, SPINECATH® AUTOTEMP® mode is entered, if the recognized probe is a Decompression Catheter, Decompression AUTOTEMP® mode is entered, and if the recognized probe is a Denervation Probe, the stimulate mode is entered.

The generator includes a processor (not shown) running software that recognizes which type of probe 165 is being connected to the generator by reading a sensor in the handle of the probe 165. The processor can be, for example, a microprocessor. The processor is capable of responding to and executing instructions in a defined manner. The software can include a program, a piece of code, an instruction, a device, or a combination of these for independently or collectively instructing the processor to interact and operate as described. The software can be embodied permanently or temporarily in various types of machines, components, physical or virtual equipment, storage media, or propagated signals capable of providing instructions to the processor. The processor typically has an associated memory (not shown), such as an internal or external memory, for storing data and programs. In one implementation, the processor can access programs externally stored in and/or performed by one or more device(s) external to the processor. The processor can include a single processor or multiple processors.

The generator also includes a probe recognition circuit (not shown) that is configured to recognize a probe that is connected to the generator. In one implementation, the probe recognition circuit can recognize a probe by recognizing a resistance value of the probe. Different probes may be have different resistance values or ranges of resistance values. In one implementation, the probe recognition circuit measures a voltage that corresponds to a resistance value. The probe recognition circuit can convert the measured analog voltage into a digital value. In one implementation, the probe recognition circuit includes a feature to identify the probe based upon the digital value. In another implementation, the probe recognition circuit supplies the digital value to the processor and the processor identifies the probe.

When the probe 165 is connected to the generator 100, the generator 100 automatically switches to the appropriate mode, resets a timer, and sets default values for the selected mode (step 420). Switching to the appropriate mode can include selecting a maximum allowed power output based on the recognized probe. The maximum allowed power for the recognized probe typically is less than the maximum power output of the generator. In one implementation, the processor controls the switching of the mode, the resetting of the time, and the setting of default values for the selected mode based on the recognized probe. The display 115 is updated to reflect the mode entered and the default values set (step 425). In one implementation, the processor supplies the mode entered and the default values to the display. The operator can change the default settings from the preset values using the soft keys and/or arrow keys (step 430). In one implementation, the soft keys and/or arrow keys are connected to provide an input to the processor to change the default settings. The display is updated (step 435) to reflect the values set by the operator. In one implementation, the processor supplies the values set by the operator to the display. The operator then performs the desired surgical procedure (step 440). During the surgical procedure, the operator may change the mode, if allowed (step 445). For example, when in stimulation mode, the operator can change between a motor stimulation mode and a sensory stimulation mode, and can change from a stimulation mode to RF lesion mode or pulsed RF mode. If the mode is changed, then steps 420–440 are repeated as described above for the new mode.

SPINECATH® AUTOTEMP® Mode

Figure 5:
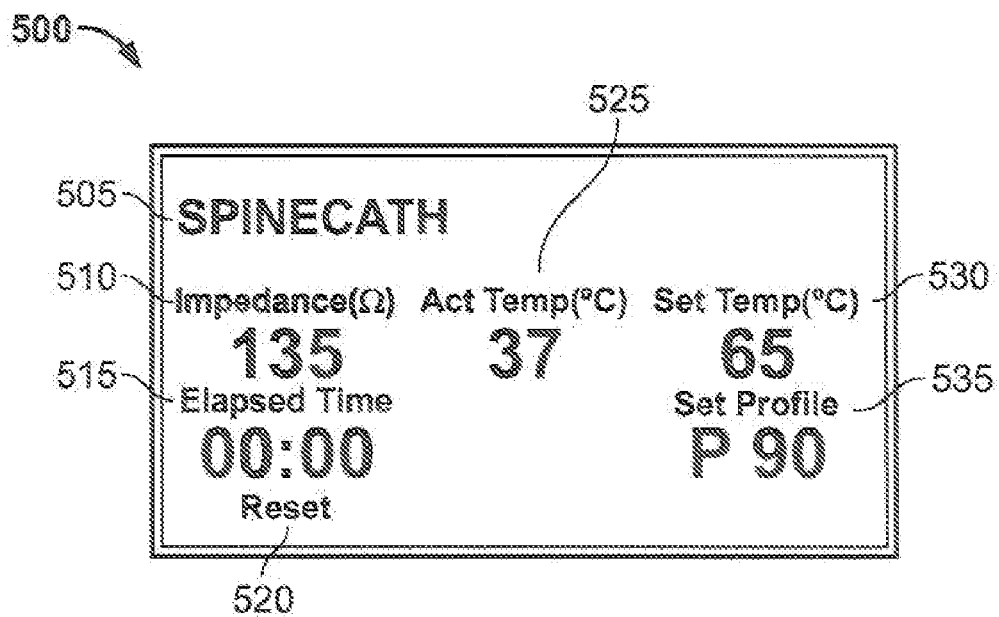
FIG. 5 is an exemplary SPINECATH® AUTOTEMP®D mode interface implemented by the electrosurgical generator of FIG. 1 while executing the processes of FIGS. 4, 11, 12, and 13.

Referring to FIG. 5, when the recognized probe is a SPINECATH®, the generator enters SPINECATH® AUTOTEMP® mode and user interface (UI) 500 is presented to the operator on display 115. User interface 500 indicates the generator mode as the SPINECATH® mode 505. Several parameters for the SPINECATH® mode are displayed to the operator. For example, the measured probe impedance 510, elapsed procedure time 515, actual probe temperature 525, set temperature 530, and set temperature profile 535 are displayed.

The actual probe temperature 525 is measured by a temperature sensing device, such as a thermocouple in the probe. The set temperature 530 is a target temperature that the generator 100 attempts to achieve and hold. The set temperature 530 can be entered manually by the operator or adjusted automatically by the generator 100. For example, the set temperature 530 can be changed manually using arrow keys 230 or can be adjusted automatically by the generator 100 while executing a set profile 535. Typically, a manual entry of set temperature 530 overrides an automatic adjustment of set temperature 530. The set profile 535 is a peak temperature that is to be achieved by the generator 100 for a predetermined duration of time. The generator 100 increases the temperature in a controlled manner until the peak temperature is achieved, and dwells at the peak temperature for a predetermined dwell time. Multiple profiles can be stored, and a particular profile selected manually by the operator or automatically by the generator. The set profile can be changed manually using arrow keys 235, or set automatically by the generator using a default setting or based upon other criteria. The operator also has a control 520 to reset the timer and set temperature using soft key 205. Typically, the reset control 520 may be activated only after a pause in the delivery of RF energy. When reset, the timer re-zeroes, the set temperature 530 returns to the default value, and the set profile 535 remains unchanged.

An exemplary set of profiles is shown below in Table 1. The profiles include information about a peak temperature, the time required to achieve the peak temperature, the dwell time at the peak temperature, and the total treatment time. By manipulating arrow keys 235, the operator can change the set profile, and the profile set by the operator will perform according to the values shown in Table 1. In the SPINECATH® auto-temperature mode, the set profile 535 typically defaults to the profile "P90", which corresponds to a peak temperature of 90° C. Other implementations are possible, and the values in Table 1 are meant to be exemplary.

The generator 100 automatically ramps up the actual probe temperature in a controlled manner up to the peak temperature shown in Table 1 for the set profile 535, and then dwells for the given dwell time at the peak temperature according to the profile. The set temperature 530 is the temperature at which the controlled ramp up is started. The set temperature 530 is initialized to a default value and is incremented by the generator in a controlled manner until the set temperature equals the peak temperature. As the generator automatically increments the set temperature, the displayed value of set temperature 530 in display 115 also is incremented.

For example, the parameters may include a default temperature profile "P90," a default value of the set temperature of 65° C., and a measured probe temperature below 65° C. In this case, the generator initially increases the temperature up to a value of 65° C. by, for example, applying full power until the set temperature of 65° C. is achieved. Full power can be a maximum allowed power for a given probe, or may be the maximum power that can be supplied by the generator. Once delivery of RF power has begun the elapsed procedure time clock 515 begins counting up. When a probe temperature of 65° C. is reached, the generator follows a ramped profile which is usually defined by a temperature increment per unit time, e.g., 1° C. every 30 seconds. The temperature ramp typically is discontinuous because the temperature increment (e.g., 1° C.) often is achieved more rapidly than the increment of unit time allotted until the temperature increment (e.g., more rapidly than 30 seconds). In other words, the generator affects the 1° C. temperature increase much more quickly than 30 seconds, and the remainder of the 30 second period before the next increase is spent at the newly achieved temperature. A ramped profile that increments the temperature 1° C. every 30 seconds takes 12.5 minutes to reach the peak temperature 90° C. Once the peak temperature of 90° C. is reached, that temperature is maintained for the dwell time of 4.0 minutes, as shown in Table 1. The entire profile takes 16.5 minutes of total treatment time—12.5 minutes to achieve the peak temperature and 4 minutes duration at the peak temperature. Energy delivery automatically stops upon completion of the profile. Once the procedure is complete, another procedure typically cannot be started without first removing the probe 165 and inserting a new probe. The energy delivery is started, and can be stopped if desired, by pressing the RF output on/off control 135 or the foot switch (not shown).

The profiles are chosen to balance patient comfort against overall treatment time, and typically are derived experimentally. If the probe temperature is raised rapidly, the overall treatment time is decreased. However, it may be more likely to cause patient discomfort.

Because the tolerance of individuals will vary, the temperature may be raised more rapidly or more slowly than the exemplary profiles described herein.

In another implementation, the maximum power allowed for the particular probe is applied until the measured temperature is equal to or within a specified value, such as, for example, 1° C., of the target temperature. When the difference between the target temperature and the measured temperature is equal to or less than the specified value, a control routine, such as a proportional-integral ("PI") routine, proportional-integral-derivative ("PID") routine, or other suitable routine, is used to control to the target temperature by adjusting the output voltage of the generator. However, when the difference between the target temperature and the measured temperature is greater than the specified value, no control routine is used. Instead, the maximum power allowed for the particular probe is applied while the difference between the target temperature and the measured temperature is greater than the specified value. Thus, the specified value acts as a transition point between a mode of applying the maximum power output allowed for the particular probe and a mode of controlling the temperature by using a control routine. The control routine can control, for example, the power output or the voltage output of the generator.

SpineCATH Autotemp Profiles

TABLE 1

| Selected Profile | Peak Temperature ° C. | Time to Peak (min.) | Dwell Time (min.) | Total Treatment Time (min.) |
| --- | --- | --- | --- | --- |
| P80 | 80 | 7.5 | 6.0 | 13.5 |
| P81 | 81 | 8.0 | 5.7 | 13.7 |
| P82 | 82 | 8.5 | 5.5 | 14.0 |
| P83 | 83 | 9.0 | 5.5 | 14.5 |
| P84 | 84 | 9.5 | 5.2 | 14.7 |
| P85 | 85 | 10.0 | 5.0 | 15.0 |
| P86 | 86 | 10.5 | 4.7 | 15.2 |
| P87 | 87 | 11.0 | 4.5 | 15.5 |
| P88 | 88 | 11.5 | 4.5 | 16.0 |
| P89 | 89 | 12.0 | 4.2 | 16.2 |
| *P90 | 90 | 12.5 | 4.0 | 16.5 |
| P91 | 91 | 13.0 | 4.0 | 17.0 |
| P92 | 92 | 13.5 | 4.0 | 17.5 |
| P93 | 93 | 14.0 | 4.0 | 18.0 |
| P94 | 94 | 14.5 | 4.0 | 18.5 |
| P95 | 95 | 15.0 | 4.0 | 19.0 |

*Default setting

The operator can change the selected profile using the arrow key 235 before the procedure begins or while the procedure is in progress. If the selected profile is changed, the generator automatically changes the peak temperature and the initial set temperature to the default value. For example, if the selected profile is changed before the procedure begins, the default set temperature is used and the temperature profile behaves similarly to the example above for profile P90, except that the actual values used in the profile will differ according to the selected profile. If the selected profile is changed while the procedure is in progress and the selected profile corresponds to a higher peak temperature, the generator 100 continues to increase the set temperature according to the temperature ramp (e.g., 1° C. every 30 seconds) until reaching the new peak temperature in order to keep a smooth profile that increases temperature quickly with minimal patient discomfort. The dwell timer begins counting once the newly selected peak temperature is reached. If, on the other hand, the selected profile corresponds to a lower peak temperature and the new peak temperature is below the current set temperature, the set temperature value is decreased to the new peak temperature by stopping or reducing the RF energy to the probe and waiting for the actual temperature to decrease to the new peak temperature. The dwell timer begins counting when the new, lower, peak temperature is reached. If the selected profile corresponds to a lower peak temperature and the new peak temperature is above the current set temperature, the generator continues to increase the set temperature according to the ramp (e.g., 1° C. every 30 seconds) until reaching the new, lower, peak temperature. The dwell timer begins counting when the new peak temperature is reached. If the profile is changed to a new profile after the peak temperature has been reached for the current profile, the peak temperature, dwell timer, and other parameters are reset to the values corresponding to the new profile and the new profile is reached as described above.

The operator can change the set temperature 530 using the arrow keys 230 while the procedure is in progress, typically to manually expedite the temperature ramp by rapidly achieving the initial set temperature. For example, if a P90 profile is selected, the operator can change the set temperature to 80° C. and the generator 100 rapidly achieves the 80° C. setting, e.g., by applying full power until the set temperature is achieved, before starting the temperature ramp of, e.g., 1° C. every 30 seconds from the 80° C. initial set temperature to the 90° C. peak temperature. The set temperature is adjustable by 1° C. for each time a key 230a, 230b is depressed. When the set temperature is manually changed, the generator 100 tracks the new temperature. Once the manual setting is complete and the new set temperature is achieved, the generator automatically increases the set temperature 1° C. every 30 seconds until reaching the peak temperature for the selected profile.

To pause delivery of RF power, the operator presses the RF output on/off control 135. The generator stops the timer and continues to monitor and display the device parameters. To continue with the automatic temperature profile, the operator presses the RF output on/off control 135, causing the generator to restart RF delivery with the timer counting from where it left off. The procedure can be reset using soft key 205, as discussed above. Typically, the reset control 520 may be activated only after a pause in the delivery of RF energy. When reset, the timer re-zeroes, the set temperature 530 returns to the default value, and the set profile 535 remains unchanged. After resetting the procedure, RF delivery is continued by pressing the RF output on/off control 135.

Figure 11:
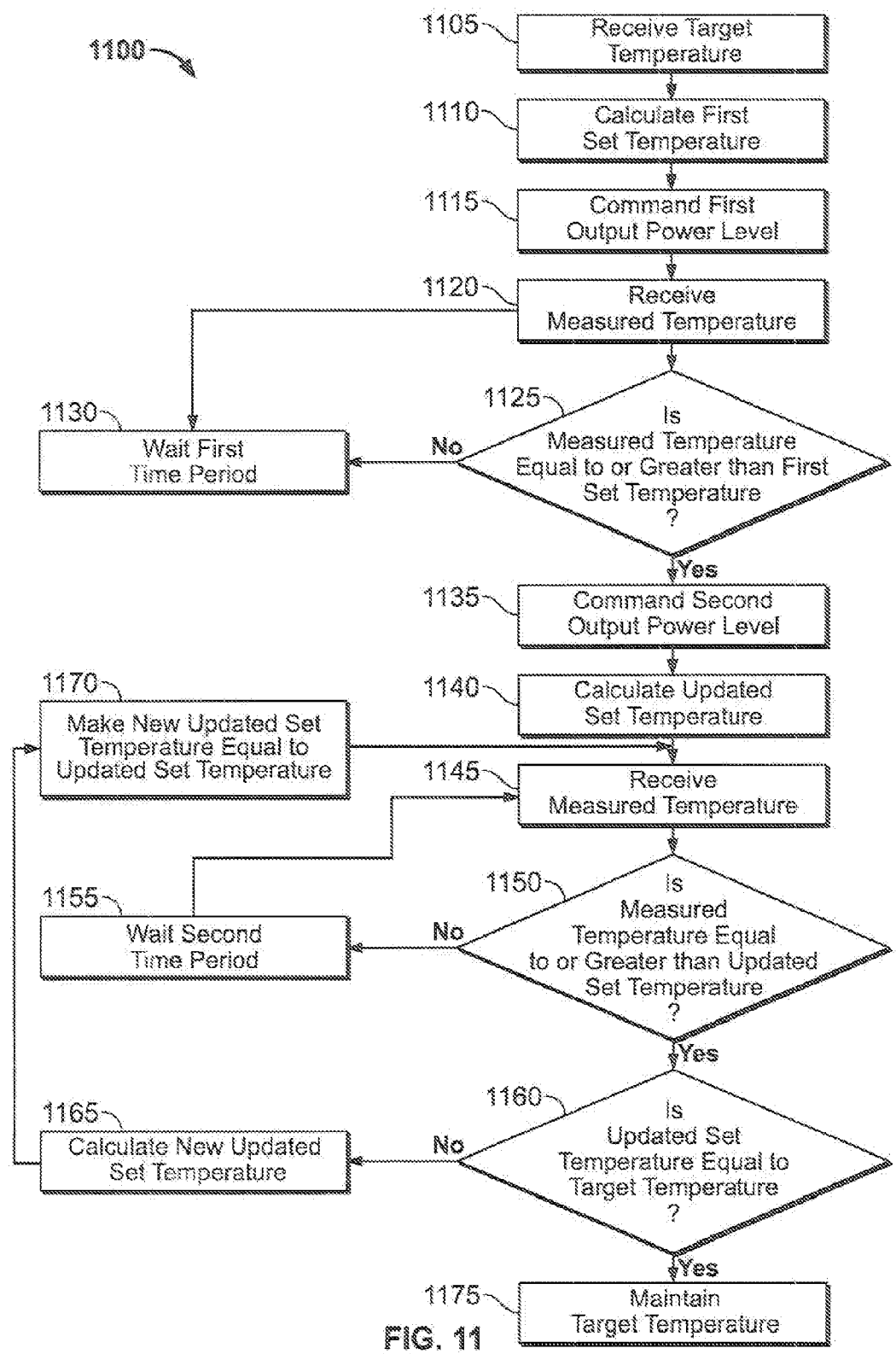

FIG. 11 shows an exemplary procedure 1100 for automatic temperature control, which may be used, for example, in the automatic temperature control of the SPINECATH® AUTOTEMP® mode described above or the Decompression AUTOTEMP® mode described below. First, a target temperature is received (step 1105). Next, a first set temperature is calculated (step 1110). The first set temperature may be calculated by subtracting a predetermined value, e.g. ten degrees, from the default value of set temperature. The default set temperature is usually 65° C. Therefore, the first set temperature typically is 55° C. (i.e., a value that is ten degrees less than the default set temperature of 65° C.).

Next, the generator 100 commands a first output power level (step 1115). The first output power level typically is full power. The generator receives a measured temperature (step 1120). If the generator determines that the measured temperature is less than the first set temperature (step 1125), then the generator waits a first predetermined period, e.g., 400 ms, (step 1130) and repeats steps 1120, 1125 and 1130 until the measured temperature is equal to (or has exceeded) the first set temperature (e.g., 55° C.).

Once the generator determines that the measured temperature is equal to (or has exceeded) the first set temperature (step 1125), e.g., 55° C., the generator commands a second power output level (step 1135). The second power level usually is a power level that will cause a temperature increase according to a desired temperature ramp profile, e.g., 1° C. every 30 seconds. The second power output level typically is less than the first power output level of step 1115. Thus, the temperature increases more slowly and in a controlled manner according to a temperature ramp profile at this point onward in the procedure 1100.

Next, the generator 100 calculates an updated set temperature (step 1140). The updated set temperature is calculated, e.g., by adding a pre-selected amount (e.g., one degree) to the first set temperature. The generator receives a measured temperature 1145. If the generator determines that the measured temperature is less than the updated set temperature (step 1150), the generator waits a second predetermined period of time, e.g., 400 ms (step 1155) and repeats steps 1145, 1150, and 1155 until the measured temperature is equal to the updated set temperature.

Once the generator determines that the measured temperature is equal to or greater than the updated set temperature, a determination is made as to whether the updated set temperature is equal to the target temperature (step 1160). If the updated set temperature is not equal to the target temperature, a new updated set temperature is calculated (step 1165). Typically, the new updated set temperature is calculated as described above with respect to the updated set temperature in step 1140. The new updated set temperature is used in steps 1145–1160. In another implementation, the set temperature is not updated and is equal to the target temperature.

Steps 1145–1160 are repeated until the updated set temperature is equal to the target temperature. Then, the target temperature is maintained (step 1175). Typically, the target temperature is maintained for the pre-selected dwell time according to temperature profile selected for the given procedure.

In another implementation, a control routine such as, for example, a PI or a PID routine can be used to adjust the output voltage to control to the measured temperature to achieve the set temperature.

Figure 12:
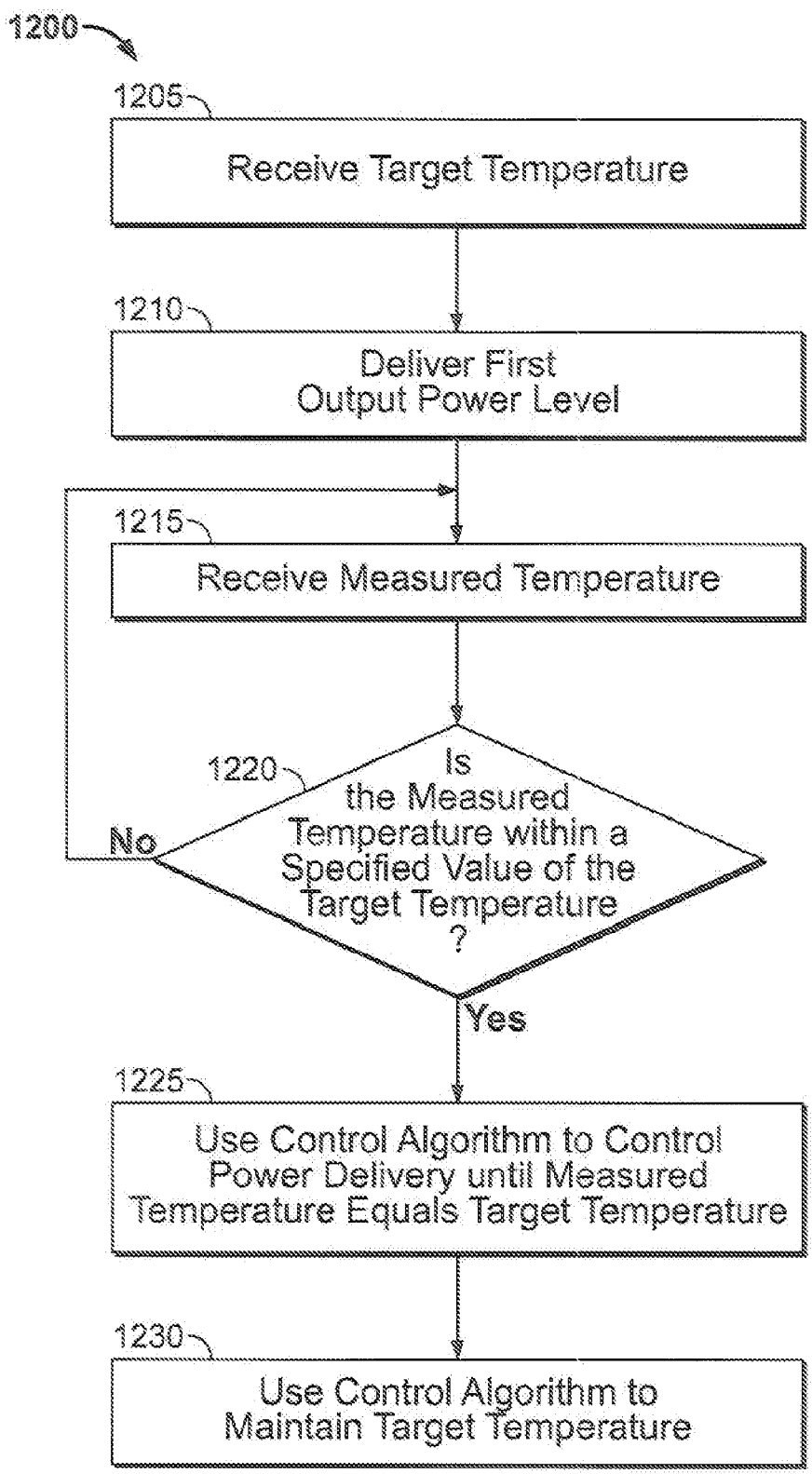

FIG. 12 shows an exemplary procedure 1200 for automatic temperature control which may be used, for example, in automatic temperature control of the SPINECATH® AUTOTEMP® mode described above or the Decompression AUTOTEMP® mode described below. A target temperatures is received (step 1205). Next, a first output level is delivered (step 1210). The first output level can be chosen based upon a recognized probe that is connected to the generator 100. Next, a temperature measurement is received (step 1215). The probe is able to measure a temperature, or the temperature measurement may be received from a different source.

A test is made to determine whether the measured temperature is within a specified value of the target temperature (step 1220). The specified value may be stored by the generator, retrieved by the generator, or calculated by the generator. In one example, the specified value may be 1° C. The specified value can vary, for example, depending upon the identity of the probe that is connected to the generator 100. If the measured temperature is not within the specified value (e.g., 1° C.) of the target temperature, the first power output level continues to be delivered until the measured temperature is within the specified value of the target temperature.

If the measured temperature is within the specified value of the target temperature, then a control algorithm is used to control power delivery by the generator (step 1225). The control algorithm calculates a second power level and controls the generator power delivery so as to make the measured temperature equal to the target temperature. The control algorithm can be a PID algorithm, a PI algorithm, or other suitable control algorithm. The control algorithm can control, for example, the output power or the output voltage of the generator 100.

In implementations using a PID (proportional-integral-derivative) control algorithm, the coefficient of the derivative term can be set to zero so that the control algorithm uses only the proportional and integral terms. In other implementations, the coefficient of the derivative term is non-zero and the control algorithm uses the derivative, proportional, and integral terms.

Also, the control values of the PID control algorithm can be pre-loaded with a starting value for the second output power level. Pre-loading a starting value for the second output power level allows for a smooth transition between the first output level and the second output level. Thereafter, the second output level typically is calculated by the control algorithm. Using a pre-loaded value for the second output level helps to ensure a more continuous transfer between the first and the second output levels. The starting value for the second output power can be derived, for example, by measuring the steady state output of the generator once the measured temperature is equal to the target temperature. The steady-state output can be measured for each type of probe that will be connected to the generator, and thereafter used as a base point for the pre-loaded value.

If the starting value for the second output level is too low, the measured temperature will drop some during transition between the first output level and the second output level, leading to an increased time required to achieve the target temperature. A low starting value also may lead to oscillations about the target temperature. Also, if the starting value is too high at the point of transition, the measured temperature can exceed the target temperature for a period of time until the control algorithm can reduce the output of the generator.

Each device used with the generator can have its own preload value for the second output level. In one example, the preloaded value is not adjusted for changes in target temperature. In another example, the preloaded value is calculated so to improve the algorithm performance. The pre-loaded value can differ depending upon the identity of the probe connected to the generator 100. The pre-loaded value can be stored in a computer readable format, or can be calculated based upon the target temperature.

Finally, the control algorithm is used to maintain the target temperature (step 1230).

Figure 13:
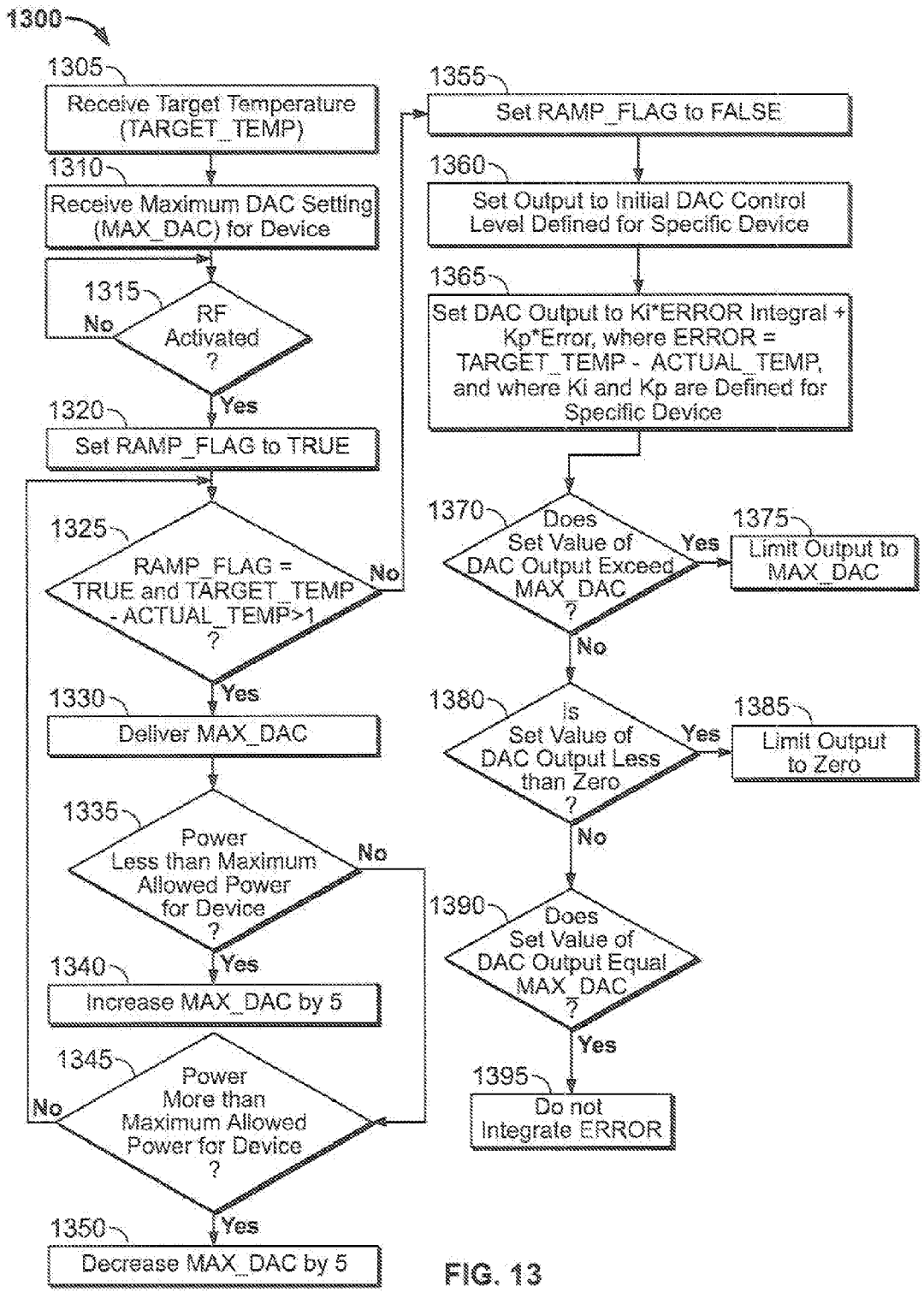

FIG. 13 shows an exemplary procedure 1300 for automatic temperature control which may be used, for example, in automatic temperature control of the SPINECATH® AUTOTEMP® mode described above or the Decompression AUTOTEMP® mode described below. In the example of FIG. 13, the RF output of the generator 100 is controlled by a digital to analog converter (DAC). In one implementation, the output value of the DAC ranges from 0 to 4095. Other output values of the DAC may be used.

A target temperature (TARGET_TEMP) is received (step 1305). Next, a maximum DAC setting (MAX_DAC) is received (step 1310). The MAX_DAC value is chosen for the particular probe being used, and the probe is installed in the electrosurgical generator 100. A check is made to determine whether RF output is activated for the generator 100 (step 1315). If the RF output is activated, then a RAMP_FLAG is set to TRUE (step 1320).

A check is made to determine: (1) if the RAMP_FLAG is set to TRUE and; (2) if the difference between the target temperature (TARGET_TEMP) and the actual temperature (ACTUAL_TEMP) is greater than 1° C. (step 1325). If both are true, then the maximum DAC setting (MAX_DAC) is delivered (step 1330). A check is made to determine if the power output is less than the maximum power output allowed for the particular probe connected to the electrosurgical generator (step 1335). The probe connected to the generator 100 may be identified, for example, in a manner similar to that discussed above with respect to the probe recognition step (step 410) of FIG. 4. After the probe is identified, a maximum power output corresponding to that probe may be retrieved from a storage location or dynamically computed. If the TARGET_TEMP and ACTUAL_TEMP difference is more than 1° C., then the maximum DAC setting (MAX_DAC) is increased by a value, such as 5 (step 1340). On the other hand, if the power is not less than the maximum allowed power for the particular probe connected to the generator, then a test is made to determine whether the power is more than the maximum allowed power for the device (step 1345). If the power is more than the maximum power allowed for the device, then the maximum DAC setting (MAX_DAC) is decreased by a value such as 5 (step 1350). If on the other hand, the power is not more than the maximum power allowed by the device, then a test is again made to determine whether the power is less than the maximum allowed power (step 1335).

Referring again to step 1325, if the difference between the TARGET_TEMP and the ACTUAL_TEMP is not greater than 1° C., then the RAMP_FLAG is set to FALSE (step 1355). Next, the output of the generator 100 is set to the initial DAC control level defined for the specific probe connected to the generator 100 (step 1360). Next, the DAC output is set to a calculated value (step 1365). The calculated value may be, for example, a value equal to Ki*ERROR Integral +Kp*ERROR, where the ERROR is the difference between TARGET_TEMP and ACTUAL_TEMP, and where Ki and Kp are defined for the specific probe connected to the electrosurgical generator.

Next, a test is made to determine whether the set value of the DAC output exceeds the MAX_DAC (step 1370). If the set value of DAC output exceeds the MAX_DAC, then the output is limited to the MAX_DAC (step 1375). On the other hand, if the set value of the DAC output does not exceed the MAX_DAC, then a test is made to determine whether the set value of the DAC output is less than 0 (step 1380). If the set value of the DAC output is less than 0, then the output is limited to 0 (step 1385). If, on the other hand, the set value of the DAC output is not less than 0, then a test is made to determine whether the set value of the DAC output equals the MAX_DAC (step 1390). If the set value of the DAC output equals the MAX_DAC, then the ERROR value, which is the difference between the TARGET_TEMP and the ACTUAL_TEMP is not integrated in the computation of the DAC output described above with respect to step 1365 (step 1295).

Decompression AUTOTEMP® Mode

Figure 6:
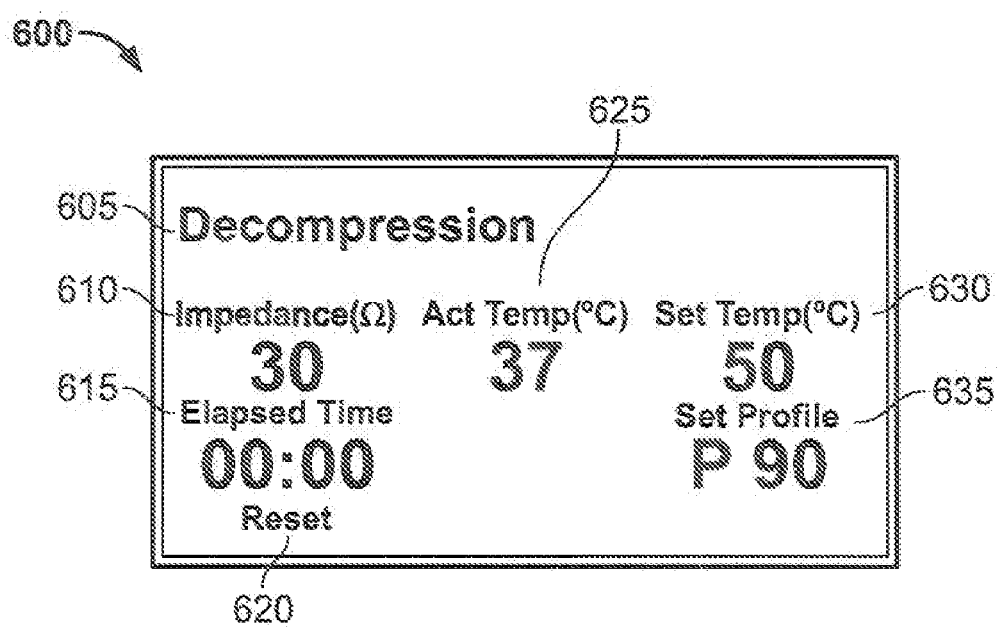
FIG. 6 is an exemplary Decompression AUTOTEMP® mode interface implemented by the electrosurgical generator of FIG. 1 while executing the processes of FIGS. 4, 11, 12, and 13.

Referring to FIG. 6, when the recognized probe is a Decompression catheter, the generator enters Decompression AUTOTEMP® mode and user interface (UI) 600 is presented to the operator on display 115. User interface 600 indicates the generator mode as the Decompression mode 605. Several parameters for the Decompression mode are displayed to the operator. For example, measured probe impedance 610, elapsed procedure time 615, actual probe temperature 625, set temperature 630, and set profile 635. A reset control 620 is activated by soft key 205. The set temperature 630 can be changed by manipulation of arrow keys 230 and the set profile 635 can be changed through manipulation of arrow keys 235. An example of possible Decompression AUTOTEMP® profiles are illustrated in Table 2. Table 2 shows the selected profile, the peak temperature, the time to achieve the peak temperature, dwell time, and the total treatment time. The decompression auto-temperature mode default profile is shown as profile "P90." In a similar manner to that discussed above with respect to FIG. 5, the generator 100 automatically increases the temperature in a controlled manner from the initial set temperature to the peak temperature, and then dwells at the peak temperature. Energy delivery stops automatically at the completion of the profile.

TABLE 2

| Selected Profile | Peak Temperature ° C. | Time to Peak (min.) | Dwell Time (min.) | Total Treatment Time (min.) |
|---|---|---|---|---|
| P80 | 80 | 3.0 | 6.0 | 9.0 |
| P81 | 81 | 3.3 | 6.0 | 9.3 |
| P82 | 82 | 3.6 | 6.0 | 9.6 |
| P83 | 83 | 3.9 | 6.0 | 9.9 |
| P84 | 84 | 4.2 | 6.0 | 10.2 |
| P85 | 85 | 4.5 | 6.0 | 10.5 |
| P86 | 86 | 4.8 | 6.0 | 10.8 |
| P87 | 87 | 5.1 | 6.0 | 11.1 |
| P88 | 88 | 5.4 | 6.0 | 11.4 |
| P89 | 89 | 5.7 | 6.0 | 11.7 |
| *P90 | 90 | 6.0 | 6.0 | 12.0 |
| P91 | 91 | 6.3 | 6.0 | 12.3 |
| P92 | 92 | 6.6 | 6.0 | 12.6 |
| P93 | 93 | 6.9 | 6.0 | 12.9 |
| P94 | 94 | 7.2 | 6.0 | 13.2 |
| P95 | 95 | 7.5 | 6.0 | 13.5 |

The set temperature 630 default typically is 50° C. for the start of the automatic temperature ramp for the decompression automatic temperature mode. The set profile default of P90 corresponds to a peak temperature of 90° C. as shown by Table 2. To begin delivery of the RF power, the operator presses RF output on/off control 135 and the elapsed procedure time clock 615 begins counting up. Once the delivery of the RF power has begun and the initial set temperature of 50° C. is achieved, the temperature is increased at a rate corresponding to a desired temperature ramp, e.g., 1° C. every 6 seconds, from 500 to a value of 80° C. Above 80° C., and until reaching the peak temperature of 90° C. for the selected P90 profile, the temperature is increase at a different desired temperature ramp, e.g., a rate of 1° C. every 18 seconds. Thus, the temperature ramp changes slope at a certain point so as to increase the temperature more slowly as the actual temperature approaches the peak temperature value. This change in temperature ramps will reduce the possibility of overshooting the peak temperature and enhances patient comfort. Upon reaching the peak temperature, the generator holds the peak temperature for a dwell time of a predetermined duration as shown in Table 2.

The values for the temperature profiles in the Decompression AUTOTEMP® mode typically differ from the values for the temperature profiles in the SPINECATH® AUTO-TEMP® mode due to differences in the probes used for each mode. As with the SPINECATH® AUTOTEMP® profiles, the Decompression AUTOTEMP® profiles are derived experimentally and balance speed of achieving the peak temperature against patient comfort.

The operator can change the set profile before or during power delivery by pressing arrow keys 235. As described above with respect to the SPINECATH® automatic temperature mode of FIG. 5, when the set profile is increased during the procedure, the generator 100 increases the set temperature according to a temperature ramp (e.g., 1° C. every 18 seconds) until reaching the new peak temperature. The dwell timer begins counting when the new peak temperature is reached. When the set profile is decreased and the new peak temperature is below the current set temperature, the set temperature value is changed to the new peak temperature and the new peak temperature is achieved as described above. The dwell timer begins counting when the new peak temperature is reached. When the set profile is decreased and the current set temperature is below the peak temperature, the generator 100 continues to increase the temperature according to the profile (e.g., 1° C. every 18 seconds) until reaching the new peak temperature. The dwell timer begins counting when the new peak temperature is reached. When the set profile is changed after the peak temperature for the current profile has been reached, the peak temperature, dwell duration timer, and other parameters are reset to the values corresponding to the new profile and the new peak temperature is achieved as described above.

The set temperature 630 can be manually changed during the auto-temperature routine using arrow keys 230. The set temperature is adjustable by 1° C. for each time the key is pressed. The temperature range typically ranges from 50° C. to the peak temperature of the selected profile. The set temperature 630 can be used, for example, to manually expedite the temperature ramp. When the initial set temperature is manually changed, the generator tracks the new set temperature and will rapidly achieve the new set temperature by, for example, applying full power until the new set temperature is reached. Once the manual setting is complete and the generator has achieved the new set temperature, the generator automatically increments the set temperature according to a desired temperature ramp (e.g., 1° C. every 6 seconds if the new set temperature is from 50° C.–80° C. and 1° C. every 18 seconds from a set temperature of 80° C. onward) until reaching the peak temperature for the selected profile.

The automatic temperature routine can be paused by depressing the RF output on/off control 135, and can be resumed by pressing RF output on/off control 135 again. Upon the continuation of the procedure, the RF power delivery commences and the timer begins counting from where it left off. The procedure can be reset by activating the reset control 620, which is activated by soft key 205. This reset action resets the timer to zero and set temperature to the default value, and leaves the profile selection unchanged. RF power delivery can be continued by pressing the RF output on/off control 135.

Sensory Stimulation Mode

Figures 7, 8:
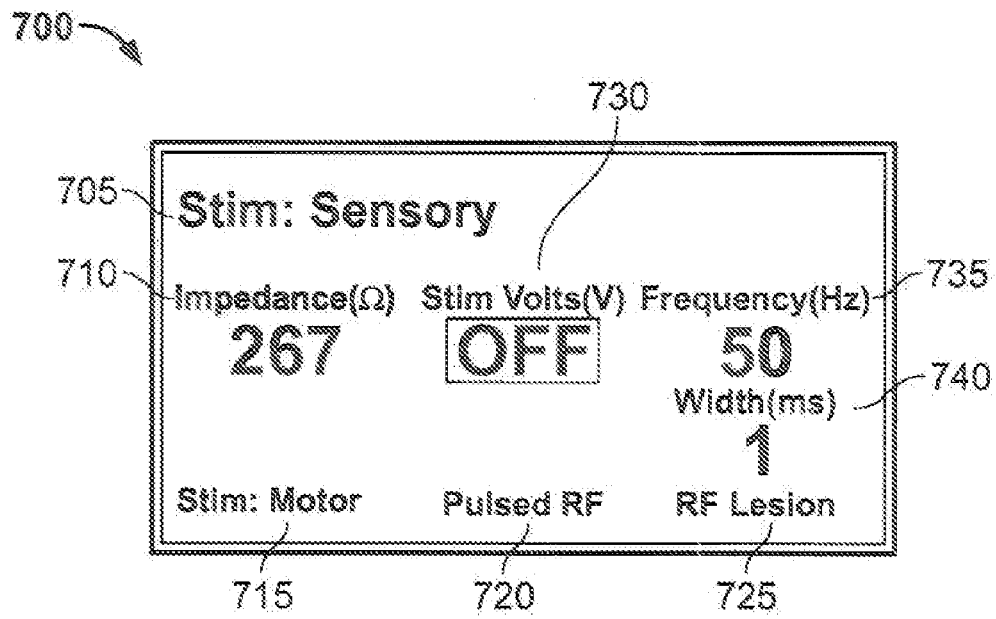
FIG. 7 is an exemplary Sensory Stimulate mode interface implemented by the electrosurgical generator of FIG. 1 while executing the processes of FIGS. 4, 11, 12, and 13.
FIG. 8 is an exemplary Motor Stimulate mode interface implemented by the electrosurgical generator of FIG. 1 while executing the processes of FIGS. 4, 11, 12, and 13.

Referring to FIG. 7, when the recognized probe is a denervation probe, the generator enters sensory stimulation mode and user interface (UI) 700 is presented to the operator on display 115. User interface 700 indicates the generator mode as the Sensory Stimulation mode 705. The sensory stimulation mode is one of two stimulations modes, sensory stimulation and motor stimulation, and each has its own default parameters. The sensory stimulation mode stimulates sensory nerves to cause a pain sensation in the patient, and the motor stimulation mode stimulates motor nerves that cause muscle movement in the patient. The stimulation modes are used to confirm proper placement of a probe in a denervation or other pain management procedure.

Upon connection of a denervation probe, the generator 100 defaults to the sensory stimulate mode as shown in UI 700. In sensory stimulation, the frequency typically defaults to 50 hertz and the pulse width defaults to 1 millisecond. The stimulation output voltage typically defaults to zero volts and is displayed as "off." Once the stimulate mode is activated, the output voltage typically starts at zero volts and may be incremented by operator action.

UI 700 shows the sensory stimulation mode 705, which includes parameters such as measured probe impedance 710, stimulation volts 730, frequency 735, pulse width 740, and controls the switching between other modes including the motor stimulation mode 715, pulsed RF mode 720, and RF lesion mode 725. The mode may be switched between the sensory stimulation and the motor stimulation modes by activation of soft key 205. The motor stimulation mode is shown and described with respect to FIG. 8. The mode may be changed between the sensory stimulation mode and the pulsed RF mode by activating soft key 215. The pulsed RF mode is shown and described with respect to FIG. 10. The mode may be changed between the sensory stimulation mode and the RF lesion by activating soft key 220. The RF lesion mode is shown and described with respect to FIG. 9. When switching between modes, a user modified parameter may be retained.

After placing the probe in the patient, the rotary encoder knob 150 is pressed once to turn the voltage on. The stimulation volts display 730 will change from "off" to zero volts. The rotary encoder knob 150 is then turned clockwise to increase the stimulate voltage from zero volts up to a maximum of 1 volt. The width of the stimulate pulses 740 may be changed using the arrow keys 235. The pulse width may be adjusted to 0.1, 0.5, 1, 2, or 3 milliseconds. In another implementation, the pulse width is not adjustable. The frequency of the pulses is typically 50 hertz for the stimulation mode 735 and is not adjustable. The voltage may be turned off by depressing the rotary encoder knob 150. Thus, the rotary encoder knob 150 acts as a "radio knob" with complete on/off and voltage increase and decrease control. Sequentially pressing the rotary encoder knob 150 toggles voltage between off and active. The active voltage is typically restarted at zero volts when switching between off and active states. When active, the voltage may be incremented up from zero volts by operator action. The voltage range for the sensory stimulation mode typically is 0–1 volt, and the pulse width range typically is 0.1, 0.5, 1, 2, and 3 milliseconds. In another implementation, the pulse width is not adjustable.

Motor Stimulation Mode

Referring to FIG. 8, if the operator enters motor stimulation mode from sensory stimulation mode, user interface (UI) 800 is presented to the operator on display 115. User interface 800 indicates the generator mode as the Motor Stimulation mode 805.

The UI 800 includes parameters such as stimulation volts 825, frequency 830, and pulse width 840. Indications are also provided to switch to a different mode including the stimulation sensory mode 810, the pulsed RF mode 815, and RF lesion mode 820. These controls are activated by using soft key 205 to switch to the sensory mode 810, soft key 215 to switch to the pulsed RF mode 815, and soft key 220 to switch to the RF lesion mode 820.

After the probe is placed in the patient, the rotary encoder knob 150 is pressed once to activate the voltage output. The output voltage defaults to 0 volts at a default pulse width value therapy profile. The rotary encoder knob 150 then is turned clockwise to increase the motor stimulate voltage from zero volts up to a maximum value, which typically is 10 volts. The width of the stimulate pulses may be changed using the arrow keys 235. The pulse width may be adjusted to 0.1, 0.5, 1, 2, or 3 milliseconds. In another implementation, the pulse width is not adjustable. The frequency of the pulse is fixed at 2 hertz for the motor stimulate mode. The voltage may be turned off at any time by depressing the rotary encoder knob 150. Sequentially depressing the rotary encoder knob 150 toggles the voltage between active and off. The active voltage is restarted at 0 volts, and may be incremented by the operator. The voltage range for the motor stimulation mode typically is 0–10 volts, the pulse width typically is adjustable but frequency typically is not, and the pulse width range typically is 0. 1, 0.5, 1, 2, and 3 milliseconds.

RF Lesion Mode

Figure 9:
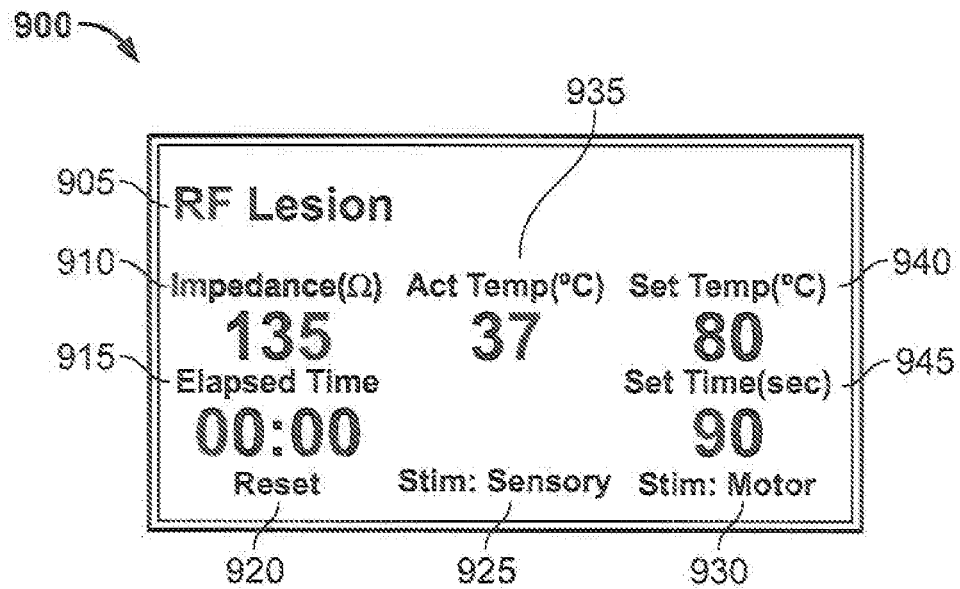
FIG. 9 is an exemplary RF Lesion mode interface implemented by the electrosurgical generator of FIG. 1 while executing the processes of FIGS. 4, 11, 12, and 13.

Referring to FIG. 9, if the operator enters RF Lesion Mode from the sensory or motor stimulation mode, user interface (UI) 900 is presented to the operator on display 115. User interface 900 indicates the generator mode as the RF Lesion mode 905. The RF Lesion mode is used to destroy tissue in a denervation procedure once the probe has been properly placed. In this mode, the generator automatically controls the power to reach and maintain a selected temperature for a selected time.

The UI 900 includes parameters such as measured probe impedance 910, elapsed procedure time 915, actual probe temperature 935, set temperature 940, and set time 945. Controls are also provided to reset the mode 920, and to switch to other modes including the sensory stimulation mode 925 and the motor stimulation mode 930. The reset control is activated by soft key 205, switching to the sensory mode is done using soft key 215, and switching to the motor stimulation mode is done using soft key 220.

The actual probe temperature reads room temperature if the probe is in free air and body temperature if the probe is inside the patient. The measured probe impedance 910 reads between 0 and 999 ohms when the denervation probe is placed in the patient. The set temperature 940 default is 80° C. for the RF lesion mode. The set temperature may be selected in a range from approximately 50° C. to 90° C. using arrow key 230. The default set time value for the RF lesion mode is 90 seconds. The timer may be set to 30, 60, 90, or 120 seconds using arrow key 235.

To begin delivery of the RF power to the probe, the operator presses the RF output on/off control 135. The elapsed procedure time display starts counting up when the RF power delivery begins. RF power delivery ceases when the elapsed procedure time reaches the set time. The RF lesion mode is exited by pressing one of the soft keys 120 across the bottom of the display that correspond to sensory stimulation mode 925 and the motor stimulation mode 930, to switch to the respective mode.

When the set temperature 940 is increased by the operator, the generator increases the actual temperature until reaching the new set temperature. When the set temperature 940 is decreased by the operator, the generator decrease the actual temperature by decreasing or stopping the RF power delivery until the actual temperature reaches the set temperature. The set time 945 may be changed by the operator to change the RF deliver time. Typically, RF power delivery is paused by pressing the RF output on/off control 135 prior to changing the set time 945. If the probe 165 is repositioned during the pause, typically the operator returns to the stimulate mode to confirm that the probe is positioned correctly prior to recommencing the denervation procedure. Upon leaving the stimulate mode and returning to the RF lesion or pulsed RF mode, the timer resets to zero. While paused, the timer may be reset by pressing the reset soft key 205 to operate control 920. This reset action will reset the elapsed procedure time and leave the set temperature selection unchanged, RF power delivery may then be continued by pressing the RF output on/off control 135.

For the RF lesion mode, the set time typically is adjusted for 30, 60, 90, and 120 seconds. The default time is usually 90 seconds. The RF lesion mode set temperature range normally is 50° C. to 90° C.

Pulsed RF Mode

Figure 10:
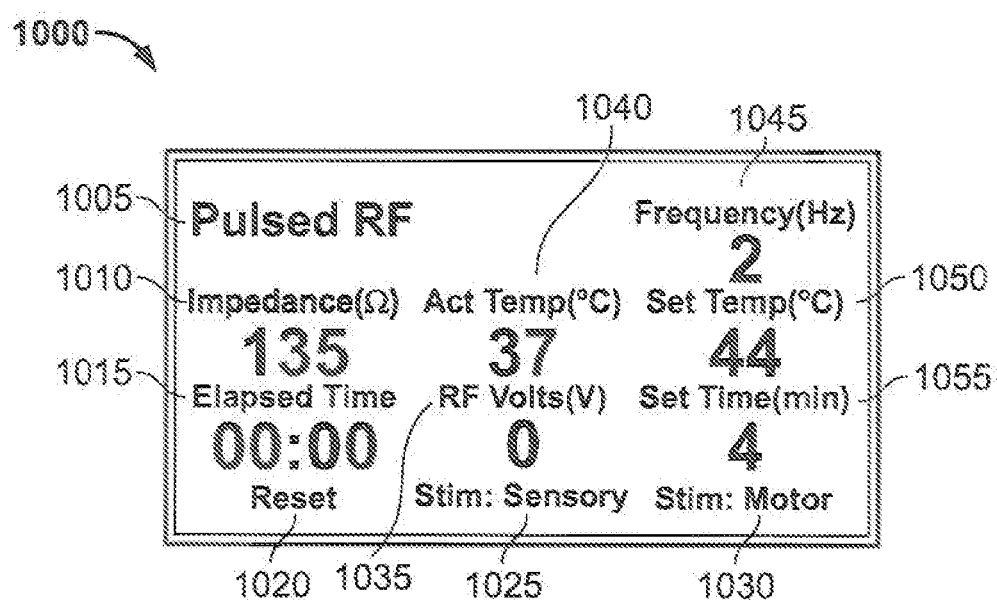
FIG. 10 is an exemplary Pulsed RF mode interface implemented by the electrosurgical generator of FIG. 1 while executing the processes of FIGS. 4, 11, 12, and 13.

Referring to FIG. 10, if the operator enters Pulsed RF Mode from sensory or motor stimulation mode, user interface (UI) 1000 is presented to the operator on display 115. User interface 1000 indicates the generator mode as the Pulsed RF mode 1005. The Pulsed RF mode is used to denature nervous tissue by exposing it to voltage.

UI 1000 includes parameters such as measured probe impedance 1010, elapsed procedure time 1015, actual probe temperature 1040, RF volts 1035, frequency 1045, set temperature 1050, and set time 1055. Controls are also provided to reset 1020 the timer, and to switch to other modes including the sensory stimulation mode 1025 and the motor stimulation mode 1030. In Pulsed RF mode, the temperature defaults to 42° C., the set time defaults to 2 minutes, the frequency defaults to 2 hertz, and the RF voltage displays zero.

In the Pulsed RF mode, the generator delivers pulsed RF energy to reach and maintain the selected set temperature for the set time. Typically, the RF pulses are approximately 20 ms in duration. The amplitude, frequency and/or pulsewidth of the pulses can be automatically adjusted to maintain the specified set temperature. In one implementation, the pulse width is not adjustable. The RF output on/off control 135 is pressed to begin delivery of RF power. The actual probe temperature reads room temperature if the probe is in free air or body temperature if the probe is placed in the patient. The measured probe impedance typically reads between 80 and 999 ohms when the denervation probe is placed in the patient. The set temperature typically is selected from a range of 35° C. to 50° C. using arrow keys 230. The frequency typically may be set to 1, 2, 4, or 8 hertz using arrow keys 225. The set time may be set to 1, 2, 3, 4, or 5 minutes using arrow keys 235.

The elapsed procedure time display 1015 starts counting up when the RF power delivery begins. The RF power delivery ceases when the elapsed procedure time reaches the set time. The Pulsed RF mode may be exited by pressing one of the soft keys on the bottom of the display corresponding to the sensory stimulation mode 1025 and the motor stimulation mode 1030. When the set temperature is increased in the pulsed RF mode, the rate of increase in temperature varies depending upon the current frequency setting. The temperature increases more slowly with a low frequency setting and more rapidly with a higher frequency setting. The rate of temperature increase typically is a function of the duty cycle of the power applied and is directly related to the frequency of pulses. When the set temperature is decreased the generator decreases the actual temperature to the set temperature by reducing or stopping the RF energy output.

RF power delivery may be paused by pressing the RF output on/off control 135. When the RF output on/off control 135 is pressed again, RF power delivery resumes. If the probe is repositioned during the pause, then the operator typically returns to the stimulate mode to confirm that the probe is properly placed prior to recommencing denervation. Upon leaving the stimulate mode and returning to the RF lesion or pulsed RF mode, the timer resets to zero. While paused, the timer may be reset 1020 by pressing the reset soft key 205. This action resets the elapsed procedure time and leave the set temperature selection unchanged. RF power delivery may then be continued by pressing the RF output on/off control 135. The set time may be changed while RF power delivery is paused using the arrow keys 235.

For the Pulsed RF mode, the set time is usually adjustable from 1 to 5 minutes. The default duration normally is 2 minutes. The Pulsed RF mode set temperature range typically is 35° C. to 50° C.

A number of implementations have been described. Nevertheless, it will be understood that various modifications may be made. For example, in the SPINECATH® AUTO-TEMP® mode and the Decompression AUTOTEMP® mode, the initial set temperature and/or the first set temperature may have a different default value for each of the different profiles. The initial set temperature and/or the first set temperature may be a fixed, pre-stored value, or it may be calculated dynamically. For example, the initial set temperature may be calculated dynamically by subtracting a predetermined value from the target temperature or by subtracting a predetermined value from the default set temperature. Also, the updated set temperature may be calculated by subtracting a pre-selected amount, e.g., ten degrees, from the target temperature or by adding a selected amount, e.g., one degree, to the initial set temperature or the first set temperature. Furthermore, other controls may be used. For example, other controls such as a switch and/or a dial may be used in place of the soft keys and the arrow keys.

In procedure 1100, certain steps may be omitted or the order of steps may be changed. For example, steps 1130 and/or 1155 maybe omitted. Also, the updated set temperature may be calculated (step 1140) prior to commanding the second power output level (step 1135).

The generator typically uses an input power source of 100–120 volts AC or 200–240 volts AC, 50 or 60 hertz. The output power is a maximum of approximately 20 watts into a 90–250 ohm load. The output power is 0–5 watts when the generator is used with the SPINECATHφ Intradiscal Catheter, 0–3 watts when the generator is used with the Decompression Catheter, and 0–20 watts when the generator is used for denervation with the RF Denervation Probe. The maximum output voltage is 160 volts RMS. In the stimulate mode, the maximum output is 10V peak. The generator uses a sine wave for the RF lesion and pulsed RF modes, and a square wave for the stimulate modes.

Accordingly, other implementations are within the scope of the following claims.

What is claimed is:

1. A computer program stored on a computer readable medium, the computer program comprising instructions for:
    a) receiving a target temperature;
    b) receiving a first generator output setting corresponding to a first generator output power;
    c) commanding the first generator output setting when a difference between the target temperature and a measured temperature is greater than a specified value;
    d) calculating a second generator output setting if the first generator output power is less than a maximum allowed generator output power for an identified surgical probe and if the difference between the target temperature and the measured temperature is greater than the specified value,
        wherein the second generator output setting corresponds to a second generator output power that is greater than the first generator output power, and
        commanding the second generator output setting;
    e) calculating a third generator output setting if the first generator output power is greater than the maximum allowed generator output power for the identified surgical probe and the difference between the target temperature and the measured temperature is greater than the specified value,
        wherein the third generator output setting corresponds to a third generator output power that is less than the first generator output power, and
        commanding the third generator output setting; and
    f) repeating c through e until the difference between the target temperature and the measured temperature is less than or equal to the specified value.

2. The computer program of claim 1 wherein instructions for receiving the target temperature comprises instructions for receiving a user input.

3. The computer program of claim 1 wherein instructions for calculating the second generator output setting comprise instructions for adding a predetermined value to the first generator output setting.

4. The computer program of claim 1 wherein instructions for calculating the third generator output setting comprise instructions for subtracting a predetermined value from the first generator output setting.

5. The computer program of claim 1 further comprising instructions for:
    g) calculating a fourth generator output setting corresponding to a fourth generator output power if the difference between the target temperature and the measured temperature is less than or equal to the specified value; and
    h) commanding the fourth generator output setting.

6. The computer program of claim 5 wherein instructions for calculating the fourth generator output setting comprise instructions for calculating the fourth generator output setting using a control algorithm.

7. The computer program of claim 6 wherein the control algorithm comprises setting the fourth generator output setting equal to a first constant multiplied by an integral of an error value plus a second constant multiplied by the error value, wherein the first constant and the second constant are defined for an identified surgical probe and the error value equals the target temperature minus the measured temperature.

8. The computer program of claim 7 further comprising instructions for limiting the fourth generator output control setting to a maximum value.

9. The computer program of claim 8 wherein the maximum value comprises the first generator output control setting.

10. The computer program of claim 8 further comprising instructions for not integrating the error value when the fourth generator control setting is equal to the maximum value.

11. The computer program of claim 7 further comprising instructions for limiting the fourth generator output control setting to a minimum value.

12. The computer program of claim 11 wherein the minimum value comprises zero.

* * * * *